(12) United States Patent
Sauer

(10) Patent No.: US 11,925,372 B2
(45) Date of Patent: *Mar. 12, 2024

(54) SURGICAL CLAMP AND CLAMP JAW

(71) Applicant: LSI Solutions, Inc., Victor, NY (US)

(72) Inventor: Jude S Sauer, Pittsford, NY (US)

(73) Assignee: LSI Solutions, Inc., Victor, NY (US)

(*) Notice: Subject to any disclaimer, the term of this patent is extended or adjusted under 35 U.S.C. 154(b) by 144 days.

This patent is subject to a terminal disclaimer.

(21) Appl. No.: 17/494,051

(22) Filed: Oct. 5, 2021

(65) Prior Publication Data
US 2022/0022903 A1    Jan. 27, 2022

Related U.S. Application Data

(63) Continuation of application No. 16/197,911, filed on Nov. 21, 2018, now Pat. No. 11,166,739, which is a
(Continued)

(51) Int. Cl.
*A61B 17/28* (2006.01)
*A61B 17/122* (2006.01)
(Continued)

(52) U.S. Cl.
CPC .......... *A61B 17/282* (2013.01); *A61B 17/122* (2013.01); *A61B 17/2804* (2013.01);
(Continued)

(58) Field of Classification Search
CPC . A61B 17/282; A61B 17/122; A61B 17/2804; A61B 17/1227; A61B 17/128;
(Continued)

(56) References Cited

U.S. PATENT DOCUMENTS 3,581,551 A    6/1971    Wilkinson
4,016,883 A    4/1977    Wright, Jr.
(Continued)

FOREIGN PATENT DOCUMENTS

EP    0615724    9/1994
EP    1654992    1/2008

OTHER PUBLICATIONS

VITALITEC Product Literature, Cygnet Flexible Clamps, copyright 2003, 10 pages.
(Continued)

*Primary Examiner* — Sarah A Long
(74) *Attorney, Agent, or Firm* — Michael E. Coyne

(57) ABSTRACT

A surgical clamp jaw is disclosed, having an inner profile and a deflection control profile opposite the inner profile. In one embodiment, the inner profile has a first substantially concave profile in an unclamped position and a second substantially flat profile in a clamped position. In one embodiment, the deflection control profile has one or more sets of corresponding abutment surfaces, at least one set of which is not contacting each other when the inner profile is in the unclamped position and which is contacting each other when the inner profile is in the clamped position. In one embodiment, the surgical clamp jaw defines one or more flexion assistance voids, wherein at least one of the one or more flexion assistance voids is in contact with a gap between one of the one or more sets of corresponding abutment surfaces.

9 Claims, 18 Drawing Sheets

Related U.S. Application Data continuation of application No. 14/207,813, filed on Mar. 13, 2014, now Pat. No. 10,219,817.

(51) Int. Cl.

| | |
|---|---|
| A61B 17/00 | (2006.01) |
| A61B 17/12 | (2006.01) |
| A61B 17/128 | (2006.01) |
| A61B 17/29 | (2006.01) |
| A61B 90/00 | (2016.01) |

(52) U.S. Cl.
CPC ............ *A61B 2017/00309* (2013.01); *A61B 2017/0046* (2013.01); *A61B 2017/00946* (2013.01); *A61B 2017/12004* (2013.01); *A61B 17/1227* (2013.01); *A61B 17/128* (2013.01); *A61B 2017/2808* (2013.01); *A61B 2017/2829* (2013.01); *A61B 2017/2923* (2013.01); *A61B 2017/2945* (2013.01); *A61B 2090/034* (2016.02); *A61B 2090/0807* (2016.02)

(58) Field of Classification Search
CPC .. A61B 2017/00309; A61B 2017/0046; A61B 2017/00946; A61B 2017/12004; A61B 2017/2808; A61B 2017/2829; A61B 2017/2923; A61B 2017/2945; A61B 2090/034; A61B 2090/0807

See application file for complete search history.

(56) References Cited

U.S. PATENT DOCUMENTS

| | | | |
|---|---|---|---|
| 4,997,436 | A | 3/1991 | Oberlander |
| 5,133,724 | A | 7/1992 | Wilson, Jr. et al. |
| 5,366,459 | A | 11/1994 | Yoon |
| 5,514,148 | A | 5/1996 | Smith, III |
| 5,618,307 | A | 4/1997 | Donlon et al. |
| 5,645,564 | A | 7/1997 | Northrup et al. |
| 5,716,370 | A | 2/1998 | Williamson, IV et al. |
| 5,776,146 | A | 7/1998 | Sackier et al. |
| 5,797,959 | A | 8/1998 | Castro et al. |
| 5,855,590 | A | 1/1999 | Malecki et al. |
| 5,921,996 | A | 7/1999 | Sherman |
| 5,964,780 | A | 10/1999 | Balazs |
| 6,036,706 | A | 3/2000 | Morejohn et al. |
| 6,146,394 | A | 11/2000 | Morejohn et al. |
| 6,368,340 | B2 | 4/2002 | Malecki et al. |
| 6,524,325 | B2 | 2/2003 | Shaw |
| 6,610,074 | B2 | 8/2003 | Santilli |
| 6,926,712 | B2 | 8/2005 | Phan |
| 6,942,676 | B2 | 9/2005 | Buelna |
| 7,108,703 | B2 | 9/2006 | Danitz et al. |
| 7,455,678 | B2 | 11/2008 | Santilli |
| 7,901,418 | B2 | 3/2011 | Danitz et al. |
| 7,963,964 | B2 | 6/2011 | Santilli et al. |
| 7,997,468 | B2 | 8/2011 | Farascioni |
| 8,156,995 | B2 | 4/2012 | Kniese |
| 8,303,611 | B2 | 11/2012 | Danitz et al. |
| 8,409,229 | B2 | 4/2013 | Wiedenbein |
| 8,444,642 | B2 | 5/2013 | Contijoch et al. |
| 8,529,585 | B2 | 9/2013 | Jacobs et al. |
| 8,888,687 | B2 | 11/2014 | Ostrovsky et al. |
| 8,998,948 | B2 | 4/2015 | Hyodo |
| 2004/0138529 | A1 | 7/2004 | Wiltshire et al. |
| 2004/0236316 | A1 | 11/2004 | Danitz et al. |
| 2004/0254606 | A1 | 12/2004 | Wittenberger et al. |
| 2005/0107667 | A1 | 5/2005 | Danitz et al. |
| 2005/0165429 | A1 | 7/2005 | Douglas et al. |
| 2006/0028041 | A1 | 2/2006 | Ono et al. |
| 2006/0116693 | A1 | 6/2006 | Weisenburgh, II et al. |
| 2006/0116697 | A1 | 6/2006 | Carter et al. |
| 2008/0172085 | A1 | 7/2008 | Chiu et al. |
| 2009/0209986 | A1 | 8/2009 | Stewart et al. |
| 2010/0063538 | A1 | 3/2010 | Spivey et al. |
| 2010/0263500 | A1 | 10/2010 | Bannasch et al. |
| 2011/0039967 | A1 | 2/2011 | Wilson et al. |
| 2011/0046437 | A1 | 2/2011 | Kassab et al. |
| 2011/0288579 | A1* | 11/2011 | Hyodo ................ A61B 17/29 606/205 |
| 2012/0037686 | A1 | 2/2012 | Hessler |
| 2012/0245598 | A1 | 9/2012 | Brown et al. |
| 2013/0274743 | A1 | 10/2013 | Banfalvi |
| 2015/0018856 | A1 | 1/2015 | Poo et al. |
| 2015/0032152 | A1 | 1/2015 | Frings |
| 2015/0164526 | A1 | 6/2015 | Bernhardt |
| 2015/0257756 | A1 | 9/2015 | Sauer |
| 2015/0257839 | A1 | 9/2015 | Vause et al. |
| 2016/0166263 | A1 | 6/2016 | Sauer |

OTHER PUBLICATIONS

Final Office Action for U.S. Appl. No. 14/207,819, filed Mar. 13, 2014, dated Nov. 30, 2016, 14 pages.

\* cited by examiner

SURGICAL CLAMP AND CLAMP JAW

CROSS REFERENCE TO RELATED APPLICATIONS

This application is a continuation of U.S. application Ser. No. 16/197,911 filed Nov. 21, 2018, which is a continuation of U.S. application Ser. No. 14/207,813 filed Mar. 13, 2014, the contents of each of which are incorporated by reference in their entirety.

FIELD

The claimed invention relates to clamping devices, and more specifically to a surgical clamp and clamp jaw.

BACKGROUND

During certain surgical procedures, it may be necessary to securely clamp and/or occlude body conduits (for example, blood vessels) of various sizes and thicknesses. Gripping or clamping instruments are often used in many types of medical procedures such as heart, lung, bariatric, and vascular surgeries. Existing clamps provide little feedback regarding how tightly the clamp is attached to a particular tissue. This can result in clamps which are holding tissue too tightly or too loosely. In the case where tissue, such as a blood vessel, is held too loosely, unexpected blood flow or blood loss may complicate a surgery, especially if the loose clamp falls off. In the case where tissue is held too tightly, the tissue may be physically damaged from an excessive clamping force and/or biologically damaged due to excessively reduced blood flow to the tissue in the region where the clamp is applied. Furthermore, depending on the design, if a surgical clamp is attached too tightly, it may have a tendency to be forced off the clamped tissue if the tissue is slippery.

In addition to clamping considerations to ensure surgical clamps are able to properly occlude body conduits, the prior art often overlooks concerns for how such clamps release. As one example, surgeons frequently use aortic cross clamps to occlude blood flow from the heart through the aorta as part of many heart surgeries, such as coronary artery bypass or aortic valve replacement surgeries. When such surgeries are near completion, and the surgeon is ready to unclamp the aorta, it may be desirable to remove the cross clamp slowly in order to avoid profound hypertension which may result from rapid reperfusion. This slow release can be difficult with some clamps as their jaws tend to create a V-shape as they are opened, thereby increasing the likelihood that the previously clamped vessel will suddenly push itself out of the clamp towards the open end of the "V", regardless of how carefully or slowly the surgeon is trying to open the clamp.

Therefore, there is a need for a surgical clamp and clamp jaw which has a reliable indication of when it is properly clamped in order to increase holding strength while reducing potential tissue damage due to excessive clamping force. Furthermore, there is also a need for a surgical clamp and clamp jaw which enables a more controlled clamp release process in order to reduce the risk of tissue damage due to pressure spikes from reestablished blood flow when clamps are removed.

SUMMARY

A surgical clamp jaw is disclosed, having an inner profile and a deflection control profile opposite the inner profile.

Another surgical clamp jaw is disclosed, having an inner profile. The inner profile has a first substantially concave profile in an unclamped position and a second substantially flat profile in a clamped position. The surgical clamp jaw also has a deflection control profile opposite the inner profile, the deflection control profile comprising one or more sets of corresponding abutment surfaces. The abutment surfaces in at least one of the one or more sets of corresponding abutment surfaces are not contacting each other when the inner profile is in the unclamped position. The abutment surfaces in at least one of the one or more sets of corresponding abutment surfaces are in contact with each other when the inner profile is in the clamped position. The surgical clamp jaw defines one or more flexion assistance voids, wherein at least one of the one or more flexion assistance voids is in contact with a gap between one of the one or more sets of corresponding abutment surfaces.

A surgical clamp is also disclosed, having a first surgical clamp jaw and a second surgical clamp jaw. The first surgical clamp jaw has a first inner profile and a first deflection control profile opposite the first inner profile. The second surgical clamp jaw has a second inner profile and a second deflection control profile opposite the second inner profile. The surgical clamp also has one or more actuators configured to create relative movement between the first inner profile of the first surgical clamp jaw and the second inner profile of the second surgical clamp jaw between an unclamped position and a clamped position.

Figure 1A:
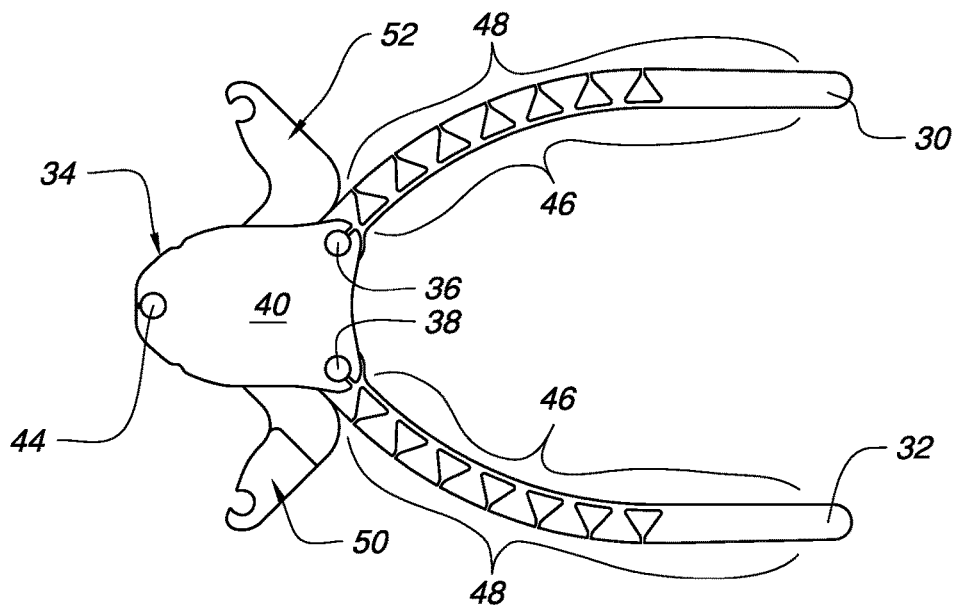
FIG. 1A is a top view of one embodiment of surgical clamp jaws pivotably held by a housing.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
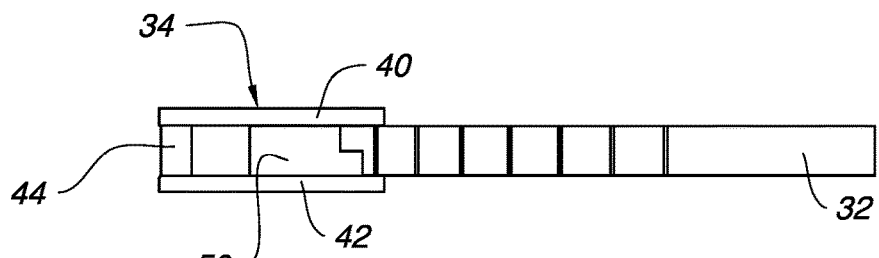
FIG. 1B is a side view of the embodied surgical clamp jaws of FIG. 1.
Figure 1C:
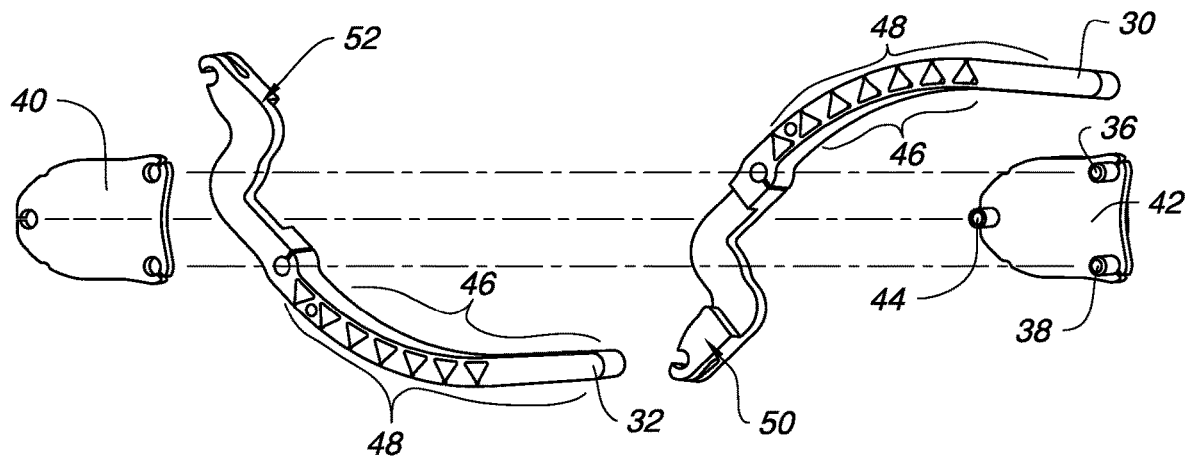
FIG. 1C is an exploded perspective view of the embodied surgical clamp jaws of FIG. 1.

FIG. 1A is a top view of one embodiment of surgical clamp jaws 30, 32 pivotably held by a housing 34. The clamp jaw 30 pivots around pivot point 36, while clamp jaw 32 pivots around pivot point 38. FIGS. 1B and 1C show the assembly of FIG. 1A in side and exploded views, respectively, in order to better illustrate the embodiment. The housing 34 in this embodiment has a top plate 40 and a bottom plate 42. In addition to locating the pivot points 36 and 38, the housing plates 40, 42 may also be coupled by one or more supports 44.

Each surgical clamp jaw 30, 32 has an inner profile 46 and a deflection control profile 48 opposite the inner profile 46. The deflection control profile 48 may be configured to allow the inner profile 46 to have one shape when the clamp jaws 30, 32 are in an unclamped position and another shape when the clamp jaws 30, 32 are in a clamped position. Various embodiments of the inner profile 46 and the deflection control profile 48 will be discussed later in this specification.

Since the surgical clamp jaws 30, 32 each are pivotable around their respective pivot points 36, 38, each jaw 30, 32 may be coupled to an actuator 50, 52 configured to rotate the respective inner profile 46 of each surgical clamp jaw 30, 32 around its respective pivot point 36, 38. Some examples of actuators 50, 52 may include, but are not limited to levers, arms, gears, pulleys, motors, or any combination or plurality thereof. Such actuators are well known to those skilled in the art and therefore, the actuators illustrated and discussed herein are often shown as simple arms, such as arms 50, 52, or the like, for simplicity. It should be understood, however, that a wide variety of actuators and their equivalents are intended to be covered herein.

In the orientation of FIG. 1A, the actuator 50 can be rotated in a clockwise arc around pivot point 36 to move surgical clamp jaw 30 in a similar direction towards surgical clamp jaw 32. Likewise, the actuator 52 can be rotated in a counterclockwise arc around pivot point 38 to move surgical clamp jaw 32 in a similar direction towards surgical clamp jaw 30. The clamp jaws 30, 32 can also be moved apart from each other by reversing the direction of the actuators.

Figure 2A:
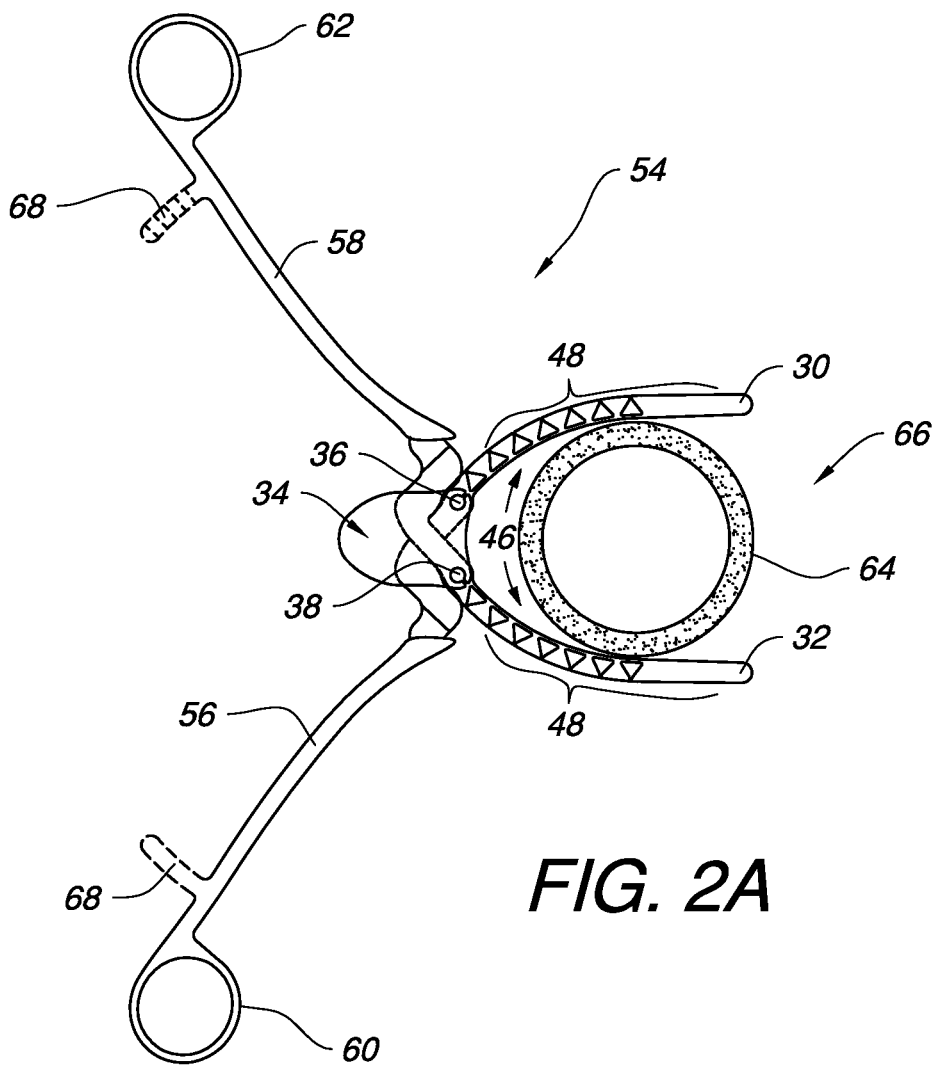
FIG. 2A illustrates one embodiment of a surgical clamp having an embodiment of the clamp jaws of FIG. 1 in an unclamped position.
Figure 15A:
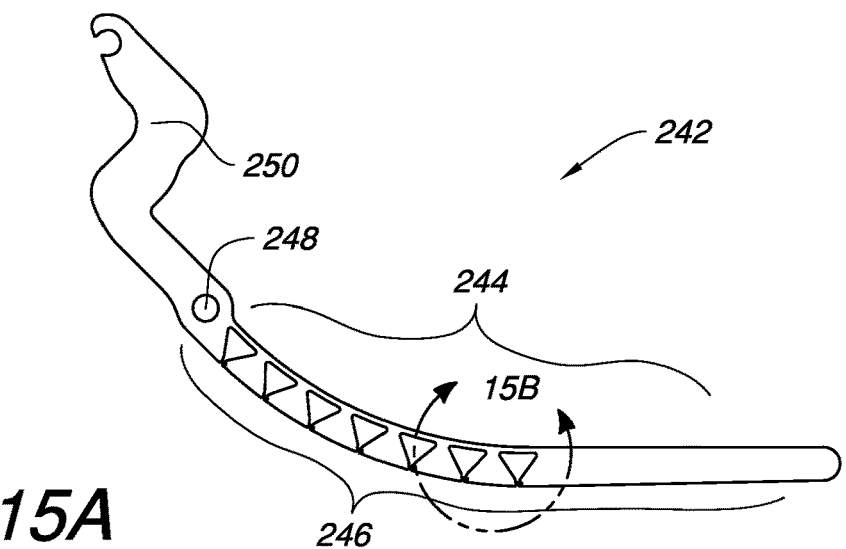
FIG. 15A illustrates another embodiment of a surgical clamp jaw having interlocking features on corresponding abutment surfaces.
Figures 1, 15B:
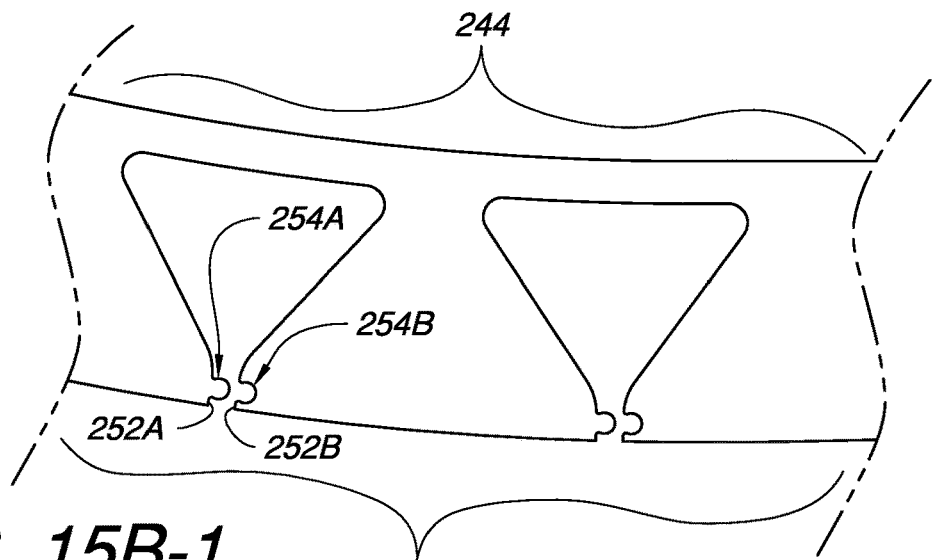
FIGS. 15B-1 and 15B-2 are enlargements of alternate embodiments of the interlocking features for a surgical clamp jaw based on the embodiment of FIG. 15A.

FIG. 2A illustrates one embodiment of a surgical clamp 54 having an embodiment of the clamp jaws 30, 32 of FIG. 1 in an unclamped position. In this embodiment, the actuators include clamp arms 56, 58 with finger holes 60, 62. The clamp jaws 30, 32 are illustrated as positioned around a conduit 64, shown in cross-section. Some non-limiting examples of conduits may include arteries, veins, other biological vessels, or even medical tubing.

When the clamp actuator arms 56, 58 are brought together, the conduit 64 receives a first clamping force nearer to the open end 66 of the clamp 54 and directed inwards because the inner profile 46 of the clamp jaws 30, 32 is substantially concave in the unclamped position. Without being tied to one particular theory, unlike conventional surgical clamps, this tends to help prevent the conduit 64 from being pushed out of the clamp 54 as the jaws 30, 32 are brought together. On reversing this action, in the process of unclamping, the concave inner profile 46 can also tend to help keep the conduit 64 from being pushed prematurely out of the clamp 54, thereby helping surgeons to have more control over how quickly or slowly the clamp is released. These benefits, enabled by the deflection control profile 48, may be helpful in allowing surgeons to avoid profound hypertension which may result from rapid reperfusion by having more control over the clamp when used as an aortic cross clamp.

Figure 2B:
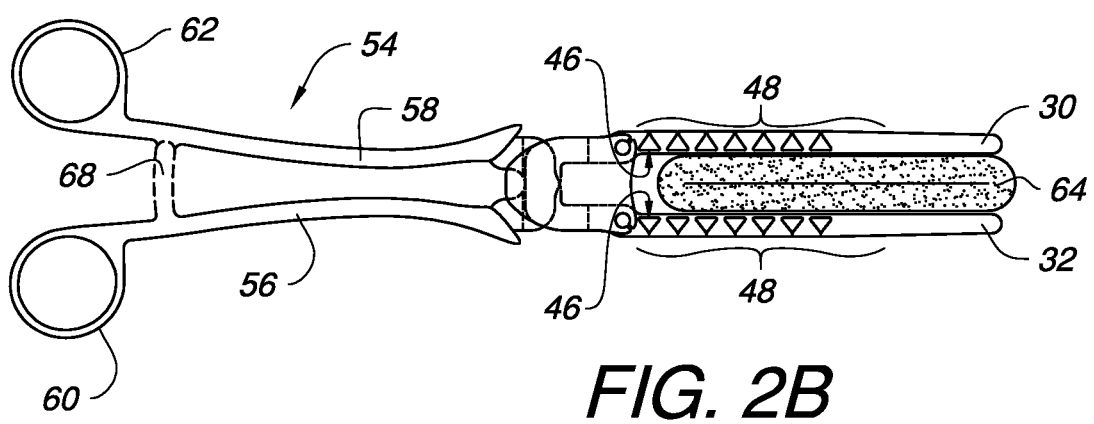
FIG. 2B illustrates the embodied surgical clamp of FIG. 2A in a clamped position.

The deflection control profile 48, as will be discussed in more detail later, allows the inner profile 46 to change shape between the unclamped position of FIG. 2A and the clamped position shown in FIG. 2B. In this embodiment, the inner profile 46 is substantially flat in the clamped position, and cannot be flexed further, thereby helping to indicate when the clamp has been properly set and to avoid the need to apply further clamping pressure. Some embodiments of the clamp 54 may also have interlocking features 68 on the actuators 56, 58 in order to help hold the clamp 54 in a closed position without the need for someone to maintain a clamping pressure.

Figure 3:
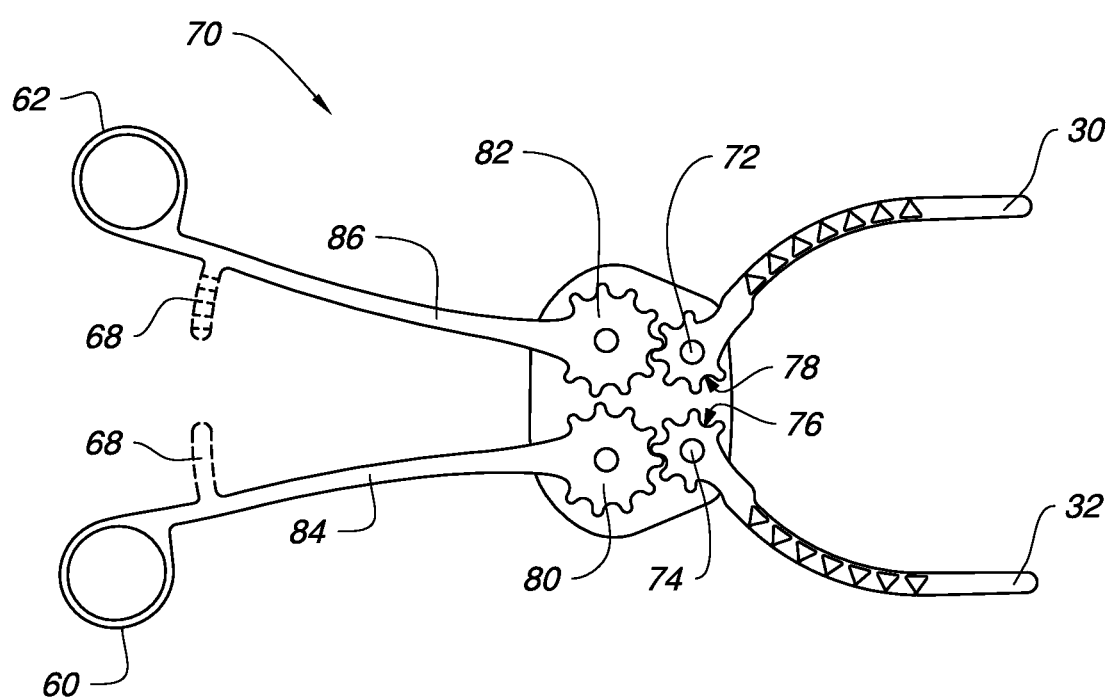
FIG. 3 illustrates another embodiment of a surgical clamp having an embodiment of the clamp jaws of FIG. 1.

The embodiments of a surgical clamp jaw disclosed herein, and their equivalents, may be used in a wide variety of surgical clamps and in a wide variety of configurations. As illustrated in FIGS. 2A and 2B, the surgical clamp jaws 30, 32 may be used in a surgical clamp 54 which has levered arms 56, 58 directly rotating the clamp jaws 30, 32 around respective pivot points 36, 38. FIG. 3 illustrates another embodiment of a surgical clamp 70 having an embodiment of the clamp jaws 30, 32 which are actuated around respective pivot points 72, 74 by gears 76, 78. In this embodiment, gears 76, 78 are driven, respectively, by gears 80, 82 coupled to arms 84, 86. Geared arrangements may be used to provide a more comfortable range of motion for the arms 84, 86 than may be available in a direct lever arrangement. As will be familiar to those skilled in the art, the gear ratios may also be adjusted to provide specific mechanical advantage for the person operating the clamp 70.

Figure 4A:
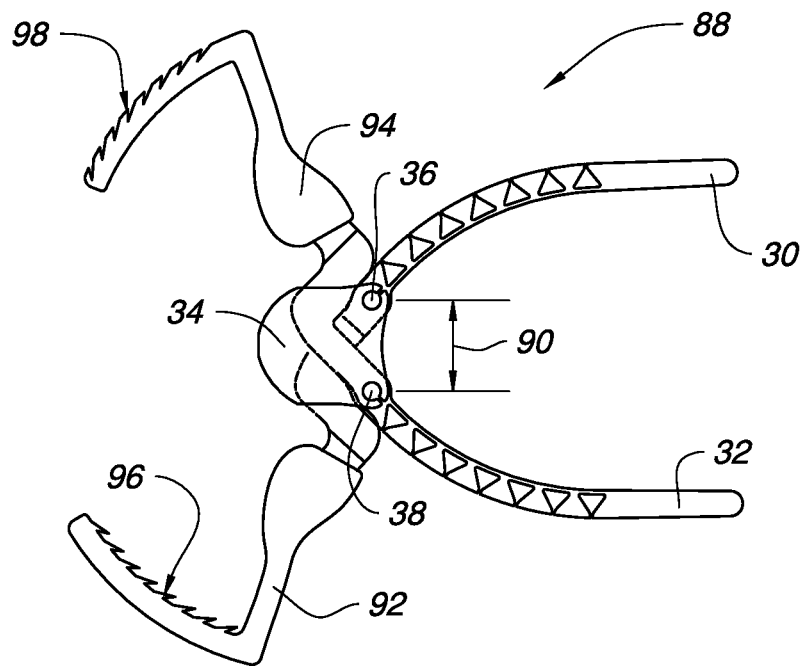
FIG. 4A illustrates another embodiment of a surgical clamp having an embodiment of the clamp jaws of FIG. 1.

The surgical clamp jaws 30, 32 may also be used in clamp embodiments which are more of a clip style clamp (a clamp which does not have finger holes and which may have shorter actuator arms), as illustrated the embodiments of FIGS. 4A-4D. FIG. 4A illustrates an embodiment of a surgical clamp 88 having an embodiment of the clamp jaws 30, 32 of FIG. 1. The features of these clamp jaws 30, 32 have been discussed previously, but it is worth noting in the embodiment of FIG. 4A that the surgical clamp jaws 30, 32 are pivotable around respective pivot points 36, 38. In this embodiment, these pivot points 36, 38 do not share a common pivot axis. Instead, the pivot points 36, 38 are separated by a pivot separation distance 90. While not necessary in all embodiments, this separation distance 90 can be used to help keep tissue from being pinched by the jaws 30, 32 as they are closed. The embodiment of FIG. 4A also has actuators 92, 94 with ratcheting surfaces 96, 98 for enabling the clamp 88 to be locked. The ratchet surfaces 96, 98 can also be deflected apart to release the clamp 88.

Figure 4B:
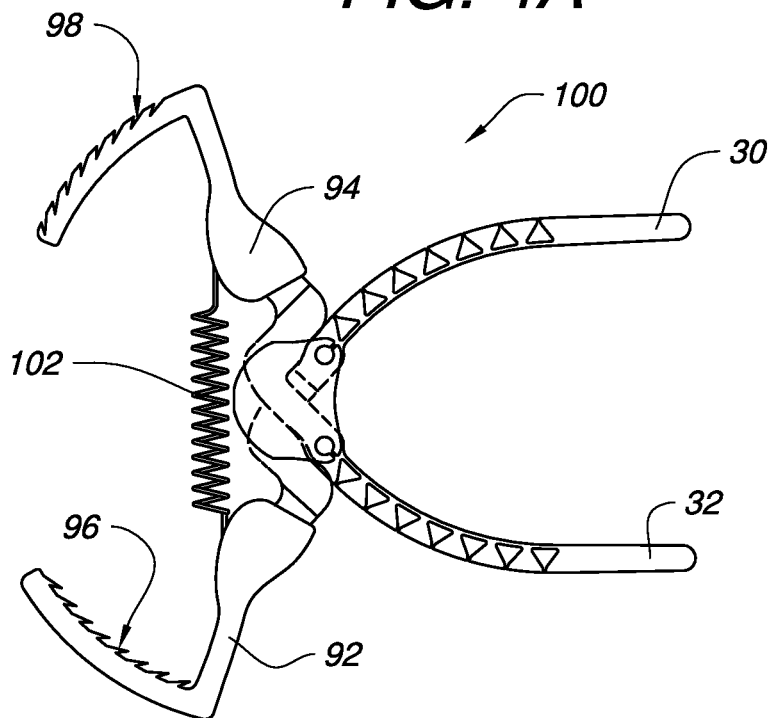
FIG. 4B illustrates an embodiment of the surgical clamp of FIG. 4A with a spring biasing element.

FIG. 4B illustrates another embodiment of a surgical clamp 100. This surgical clamp 100 is similar to the clamp of FIG. 4A, the features of which have been discussed previously. The clamp 100 of FIG. 4B, however, also includes a spring biasing element 102. Depending on the embodiment, the spring biasing element 102 could be configured to help push the actuator arms 92, 94 apart or pull them together, thereby enabling the jaws 30, 32 of clamp 100 to be biased open or closed. Spring biasing element 102 is drawn schematically since there are a wide variety of springs or spring elements which could be used to for biasing element 102. Such spring elements are well known to those skilled in the art.

Figure 4C:
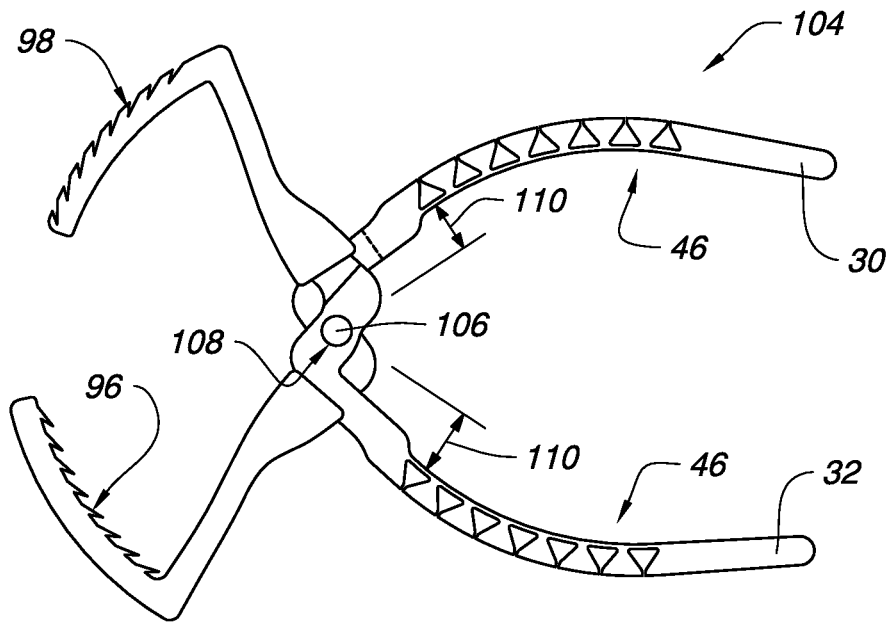
FIG. 4C illustrates another embodiment of a surgical clamp having an embodiment of the clamp jaws of FIG. 1, but with a single pivot axis.

FIG. 4C illustrates another embodiment of a surgical clamp 104. This surgical clamp 104 is similar to the clamp of FIG. 4A, the features of which have been discussed previously. The clamp 104 of FIG. 4C, however, does not have a pivot separation distance. Instead, the surgical clamp jaws 30, 32 of clamp 104 have a common pivot axis 106. Depending on the embodiment, a common pivot axis 106 can have the advantage of removing the need for a housing. In one sense, the axle 108 which provides the common pivot axis 106 can serve a similar function to the housing of previous embodiments by tying the surgical clamp jaws 30, 32 together so they can pivot relative to each other.

The embodiment of FIG. 4C also illustrates that the pivot point 106 may be offset from the inner profile 46 by an offset distance 110 in order to mitigate any pinching effect which might be caused by having a single pivot point 106. Such an offset 110 enables approximation of the benefits of dual pivot points from previous embodiments. Other embodiments with a single pivot point may not have such an offset 110.

Figure 4D:
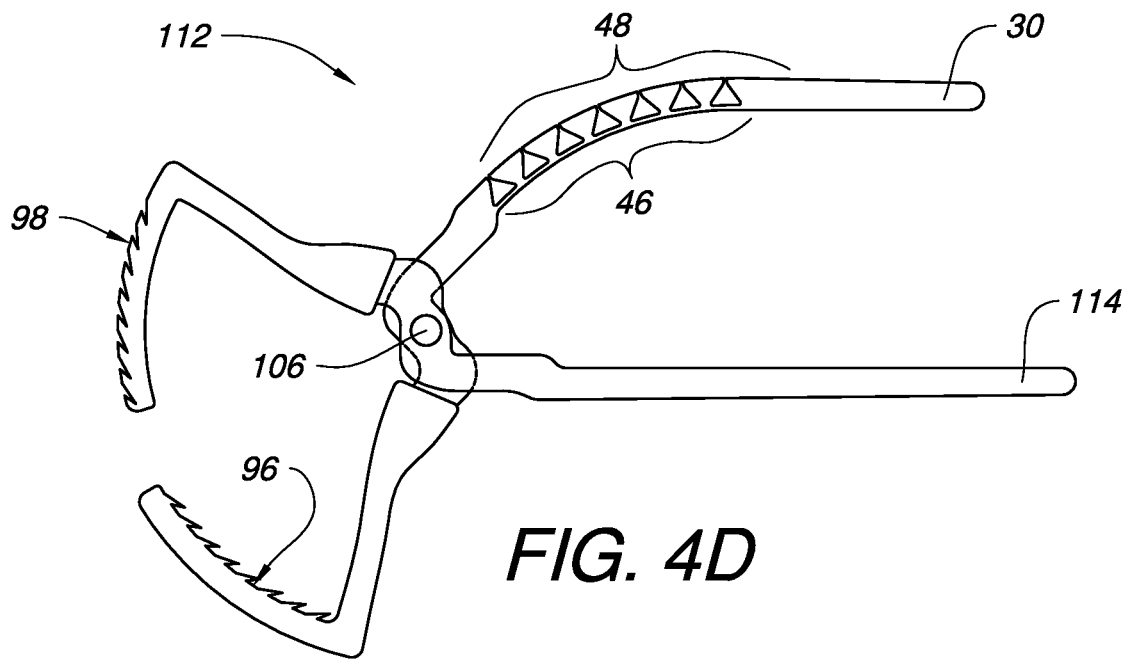
FIG. 4D illustrates a further embodiment of a surgical clamp having an embodiment of a single clamp jaw from FIG. 1.

FIG. 4D illustrates a further embodiment of a surgical clamp 112. This surgical clamp 112 is similar to the clamp of FIG. 4C in that it has a shared pivot axis 106 and actuators with ratchet surfaces 96, 98. The embodiment of FIG. 4D differs, however, in that it has one surgical clamp jaw 30 as discussed previously, while the other clamp jaw 114 has a fixed profile. In this example, the fixed profile clamp jaw 114 has a flat profile, but in other embodiments, the profile for the fixed profile clamp jaw 114 could have other shapes. In embodiments with a single surgical clamp jaw 30 which has an inner profile 46 and a deflection profile 48 opposite the inner profile 46, the substantially concave shape of the inner profile 46 in the unclamped position can still work with the fixed profile clamp jaw 114 to help contain a conduit being clamped between the jaws with similar benefits as described previously.

Figure 5A:
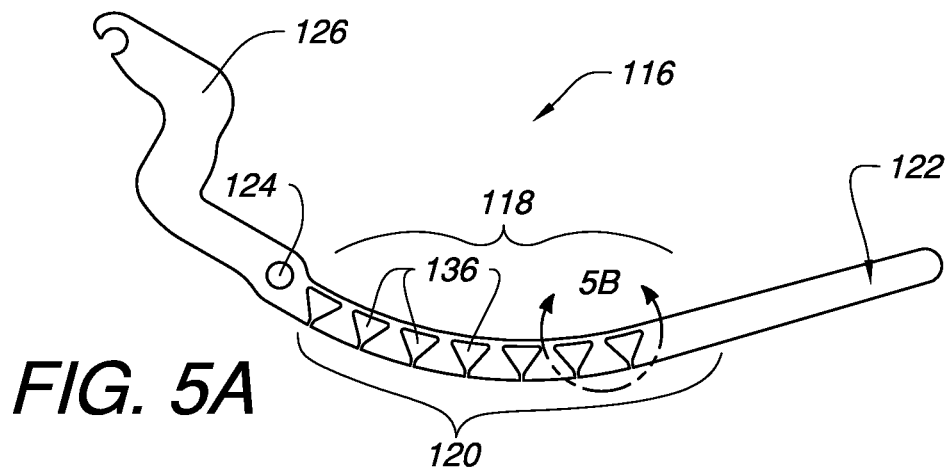
FIG. 5A illustrates one embodiment of a surgical clamp jaw in an unclamped position.

The deflection control profile 48, opposite the inner profile 46, is an important concept for the embodiments disclosed herein. FIG. 5A illustrates one embodiment of a surgical clamp jaw 116 in an unclamped position. The surgical clamp jaw 116 has an inner profile 118 and a deflection control profile 120 opposite the inner profile 118. Although a portion 122 of the clamp jaw has a straight profile in this embodiment, when taking into account the totality of the inner profile 118, the inner profile 118 still has a substantially concave profile in the unclamped position. The clamp jaw 116 also has a pivot point 124 and an arm 126 which can be used as an actuator or coupled to another actuator.

Figure 5B:
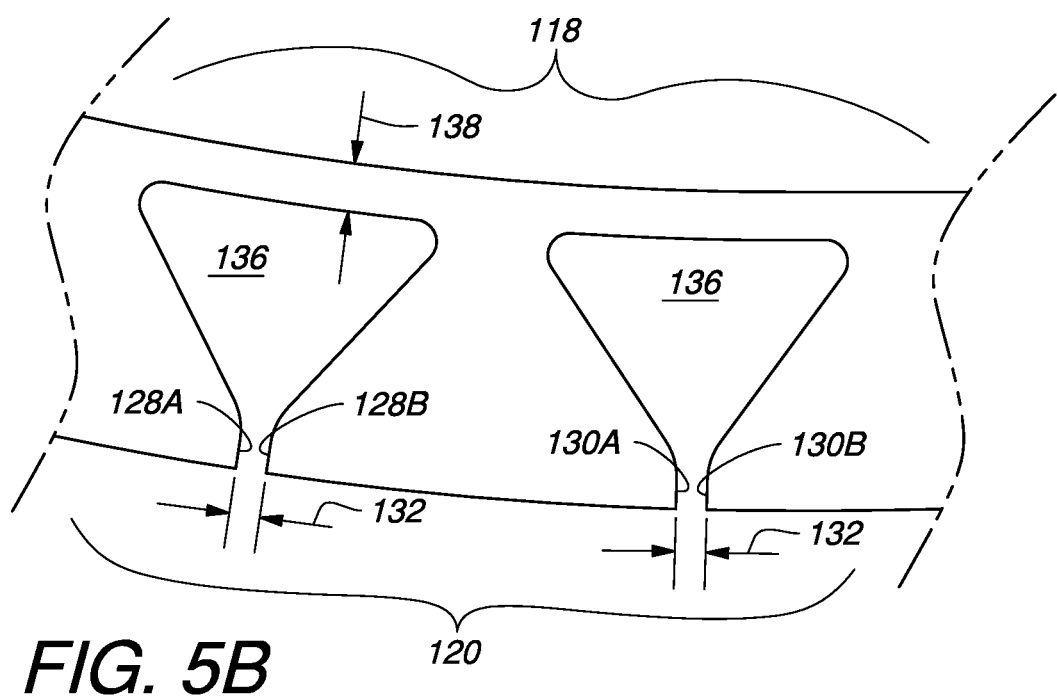
FIG. 5B is an enlarged view of a portion of the surgical clamp jaw of FIG. 5A, featuring one embodiment of corresponding abutment surfaces and one embodiment of flexion assistance voids.

In this embodiment, the deflection control profile 120 comprises one or more sets of corresponding abutment surfaces which are best seen in the enlarged view of FIG. 5B. FIG. 5B shows a first set of corresponding abutment surfaces 128A, 128B and a second set of corresponding abutment surfaces 130A, 130B. For convenience, only one set of corresponding abutment surfaces 128A, 128B will be discussed, however, it should be understood that the other sets of corresponding abutment surfaces will operate in a similar fashion. In the unclamped position shown in FIG. 5B, the set of corresponding abutment surfaces 128A, 128B are not contacting each other. Instead, they are separated by an abutment separation distance 132. Depending on the embodiment, the abutment separation distance 132 between each set of corresponding abutment surfaces 128A, 128B may be the same or different. As the surgical clamp jaw 116 is moved from an unclamped position (shown in FIG. 5A) to a clamped position (shown in FIG. 5C), the inner profile 118 will be able to deflect back towards the deflection control profile 120 until the abutment surfaces 128A, 128B come into contact with each other. A clamping force 134, from the clamp jaw 116 acting in concert with another clamp jaw (not shown, but discussed previously), acts on the clamp jaw 116 in order cause the deflection. The abutment separation distance 132 can be established to control the amount of deflection possible for the inner profile 116. Smaller abutment separation 132 will enable less deflection, while larger abutment separation 132 will enable more deflection.

Figure 5C:
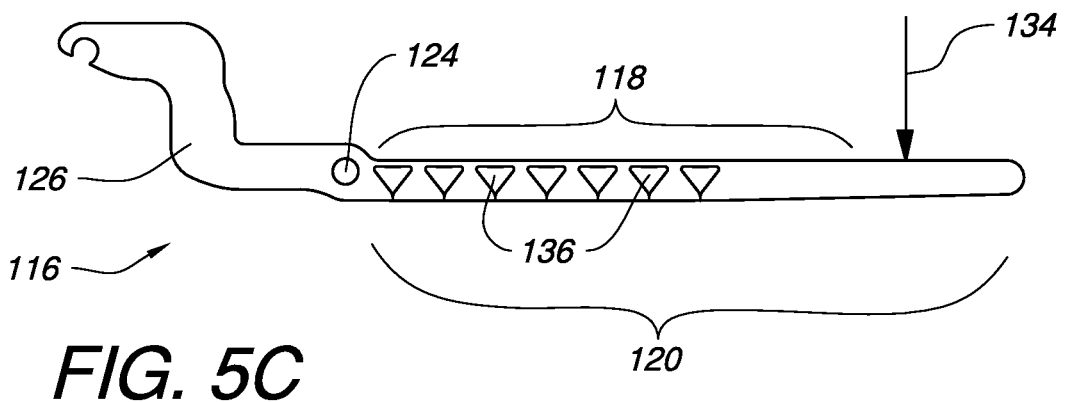
FIG. 5C illustrates the embodied surgical clamp jaw of FIG. 5A in a clamped position featuring a substantially flat inner profile.

In this embodiment, the inner profile 118 is substantially flat in the clamped position, as illustrated in FIG. 5C.

In order for the inner profile 118 to be able to deflect until the corresponding abutment surfaces 128A, 128B contact each other, some embodiments may include one or more flexion assistance voids 136. The flexion assistance voids 136 reduce the effective thickness 138 of the clamp jaw 116 in certain places behind the inner profile 118, thereby making the inner profile 118 more flexible. In the embodiment of FIGS. 5A-5C, the flexion assistance voids 136 have a substantially triangular shape, although other embodiments may use other shapes. Also, in this embodiment, each flexion assistance void 136 is in contact with the gap 132 between the set of corresponding abutment surfaces 128A, 128B. This continuity between the gap 132 and the flexion assistance void 136 may be desirable from a manufacturing point of view, but it is not necessary in all embodiments.

Figure 6A:
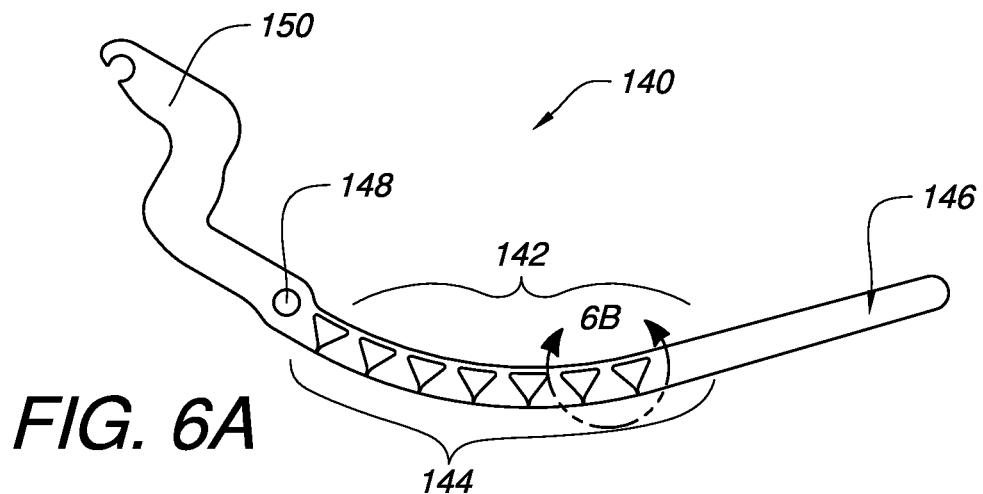
FIG. 6A illustrates another embodiment of a surgical clamp jaw in an unclamped position.

FIG. 6A illustrates another embodiment of a surgical clamp jaw 140 in an unclamped position. The surgical clamp jaw 140 has an inner profile 142 and a deflection control profile 144 opposite the inner profile 142. Although a portion 146 of the clamp jaw 140 has a straight profile, in this embodiment, when taking into account the totality of the inner profile 142, the inner profile 142 has a first substantially concave profile in the unclamped position. The clamp jaw 140 also has a pivot point 148 and an arm 150 which can be used as an actuator or coupled to another actuator.

Figure 6B:
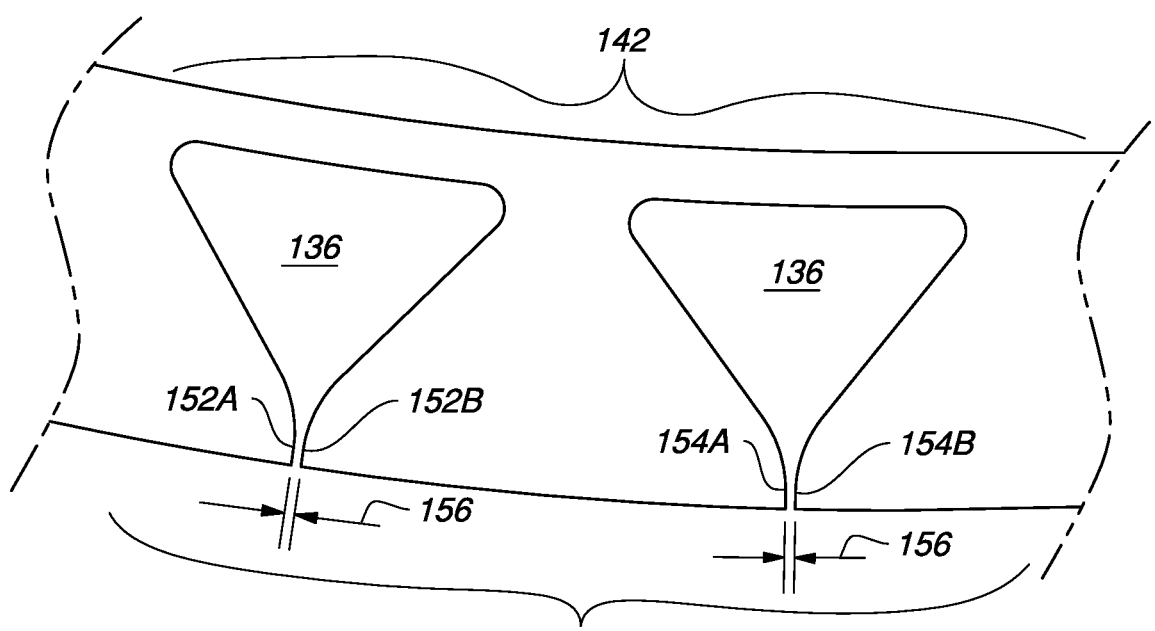
FIG. 6B is an enlarged view of a portion of the surgical clamp jaw of FIG. 6A, featuring another embodiment of corresponding abutment surfaces and one embodiment of flexion assistance voids.
Figure 6C:
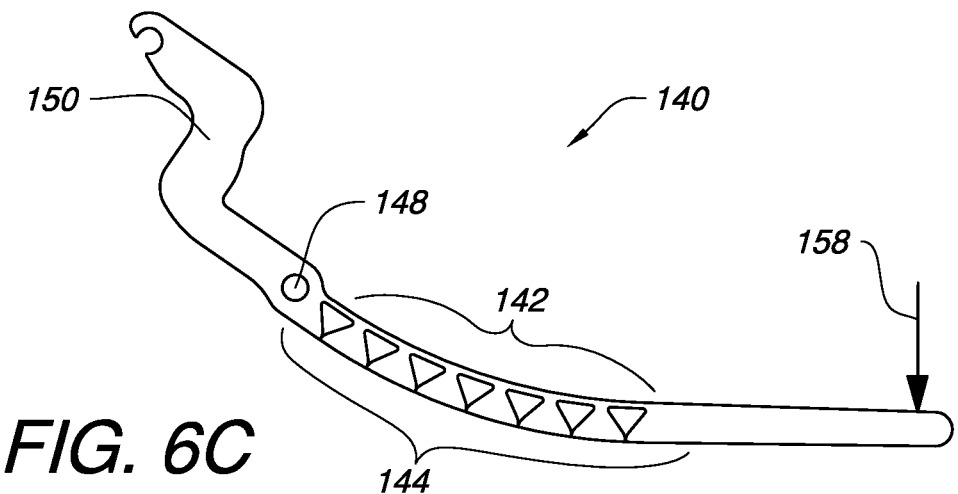
FIG. 6C illustrates the embodied surgical clamp jaw of FIG. 6A in a clamped position featuring a substantially concave inner profile.

As with the previous embodiment, in this embodiment, the deflection control profile 144 comprises one or more sets of corresponding abutment surfaces which are best seen in the enlarged view of FIG. 6B. FIG. 6B shows a first set of corresponding abutment surfaces 152A, 152B and a second set of corresponding abutment surfaces 154A, 154B. For convenience, only one set of corresponding abutment surfaces 152A, 152B will be discussed, however, it should be understood that the other sets of corresponding abutment surfaces will operate in a similar fashion. In the unclamped position shown in FIG. 6B, the set of corresponding abutment surfaces 152A, 152B are not contacting each other. Instead, they are separated by an abutment separation distance 156. The abutment separation distance 156 in the embodiment of FIGS. 6A-6C is smaller than the abutment separation distance 132 from the embodiment of FIGS. 5A-5C. As a result, by comparison, the embodiment illustrated in FIGS. 6A-6C is not able to deflect as far. Accordingly, as the surgical clamp jaw 140 is moved from an unclamped position (shown in FIG. 6A) to a clamped position (shown in FIG. 6C), the inner profile 142 will be able to deflect back towards the deflection control profile 144 until the abutment surfaces 152A, 152B come into contact with each other, resulting in the inner profile 142 having a second substantially concave profile in the clamped position of FIG. 6C. While having a concave profile in the clamped position may not be useful for completely occluding some conduits, the concave clamped profile may allow a surgeon to partially occlude a conduit. Such a clamp could be used in conjunction with a completely occluding clamp in order to help avoid sudden pressure changes inside the conduit. For example, the conduit could be partially occluded with one clamp and then completely occluded with a second clamp, each clamp having differing inner profiles in the clamped position. Near the end of the surgical procedure, the completely occluding clamp could be removed first, allowing some fluid to flow through the partially occluded clamp. This might allow the surgeon to ease the patient's related biological systems into full use as the partially occluded clamp would later be released.

As with the previous embodiment, a clamping force 158, from the clamp jaw 140 acting in concert with another clamp jaw (not shown, but discussed previously) acts on the clamp jaw 140 in order cause the deflection. The clamp jaw 140 in this embodiment also has flexion assistance voids 136, the features of which have been discussed previously.

Figure 7A:
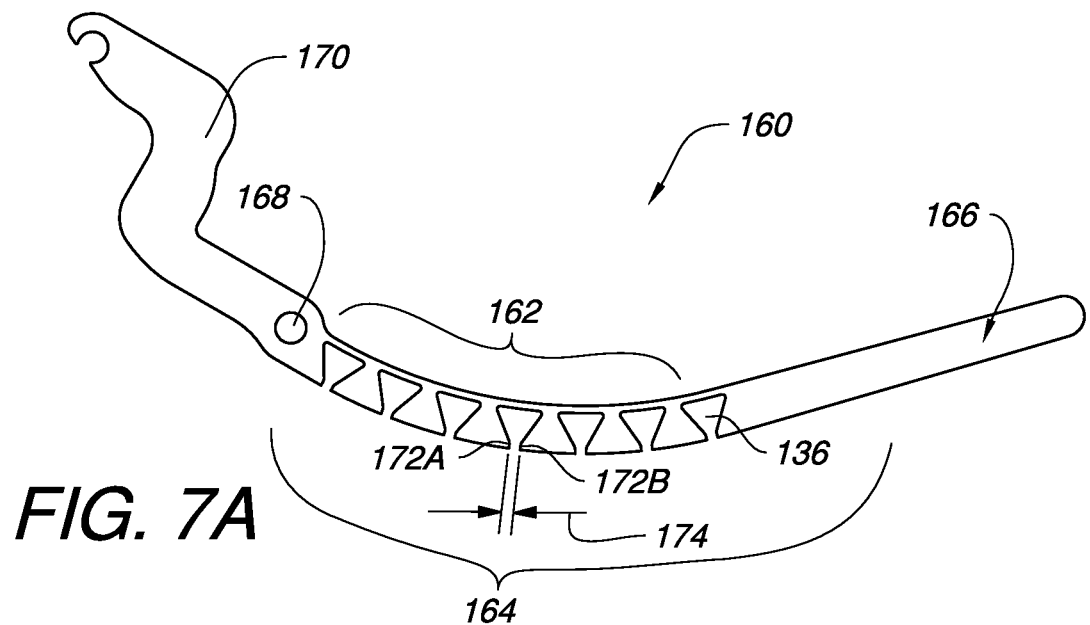
FIG. 7A illustrates a further embodiment of a surgical clamp jaw in an unclamped position.

FIG. 7A illustrates another embodiment of a surgical clamp jaw 160 in an unclamped position. The surgical clamp jaw 160 has an inner profile 162 and a deflection control profile 164 opposite the inner profile 162. Although a portion 166 of the clamp jaw 140 has a straight profile in this embodiment, when taking into account the totality of the inner profile 162, the inner profile 162 has a substantially concave profile in the unclamped position. The clamp jaw 160 also has a pivot point 168 and an arm 170 which can be used as an actuator or coupled to another actuator.

Figure 7B:
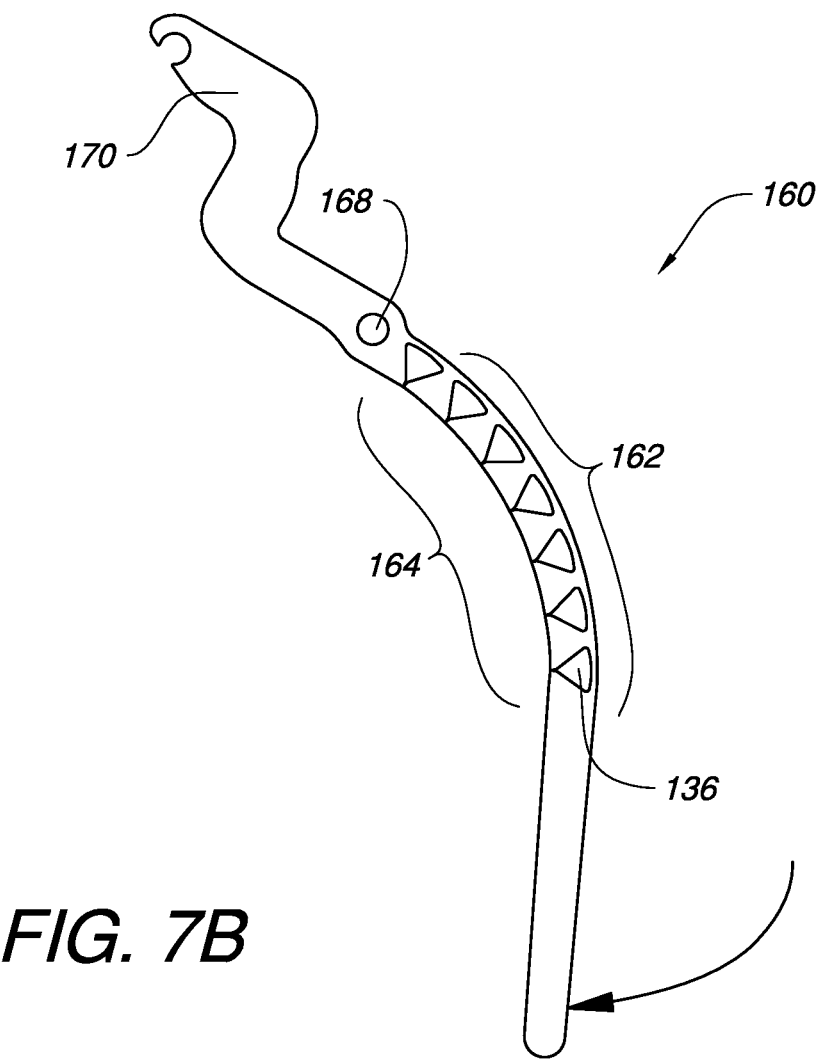
FIG. 7B illustrates the embodied surgical clamp jaw of FIG. 7A in a clamped position featuring a substantially convex inner profile.

As with the previous embodiments, in this embodiment, the deflection control profile 164 comprises one or more sets of corresponding abutment surfaces. For convenience, only one set of corresponding abutment surfaces 172A, 172B will be discussed, however it should be understood that the other sets of corresponding abutment surfaces will operate in a similar fashion. In the unclamped position shown in FIG. 7A, the set of corresponding abutment surfaces 172A, 172B are not contacting each other. Instead, they are separated by an abutment separation distance 174. The abutment separation distance 174 in the embodiment of FIGS. 7A-7B is larger than the abutment separation distance 132 from the embodiment of FIGS. 5A-5C. As a result, by comparison, the embodiment of FIGS. 7A-7B is able to deflect farther. Accordingly, as the surgical clamp jaw 160 is moved from an unclamped position (shown in FIG. 7A) to a clamped position (shown in FIG. 7B), the inner profile 162 will be able to deflect back towards the deflection control profile 164 until the abutment surfaces 172A, 172B come into contact with each other, resulting in the inner profile 162 having a substantially convex profile in the clamped position of FIG. 7B. While having a convex inner profile in the clamped position would not be useful in many situations, such a clamp might be useful where softer gripping forces are needed or where the clamp had to be used to hold or steady an unusually shaped structure. The clamp jaw 160 in this embodiment also has flexion assistance voids 136, the features of which have been discussed previously.

Figure 8:
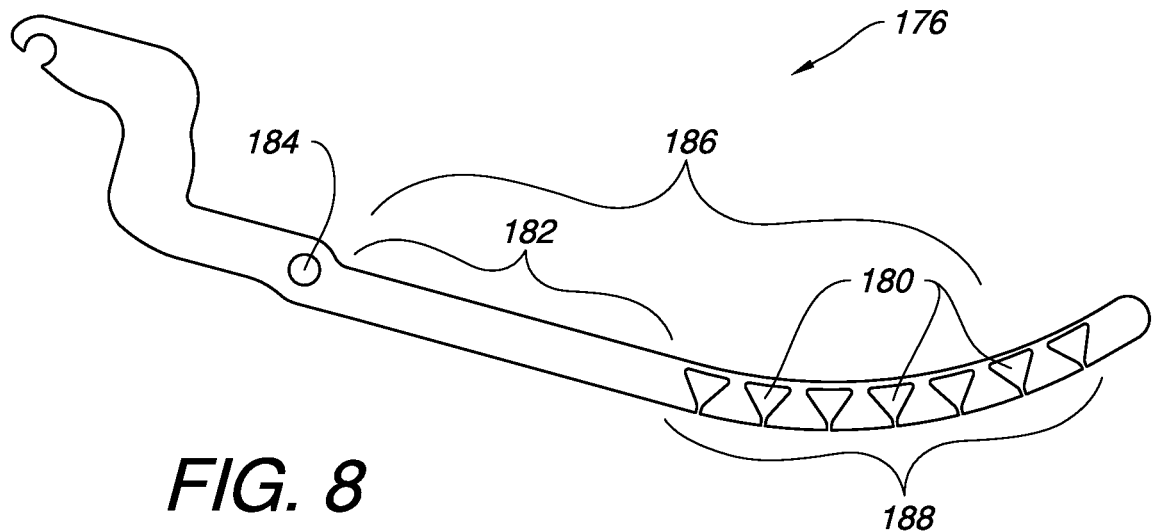
FIGS. 8 and 9 illustrate other embodiments of surgical clamp jaws having examples of different flexion assistance void distribution.
Figure 9:
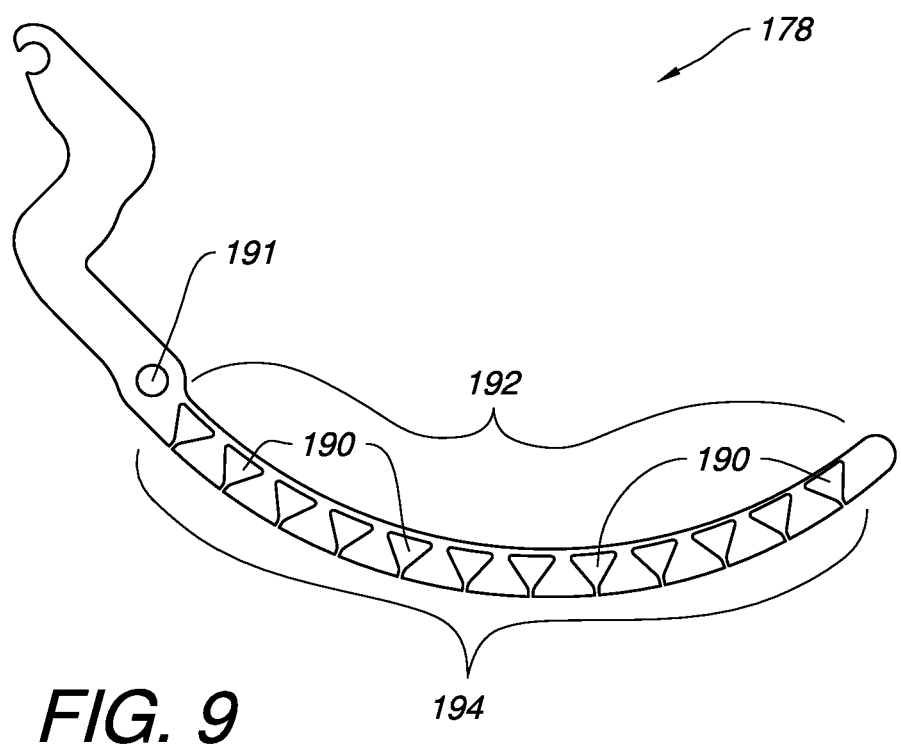

In the embodiments discussed up to this point, the flexion assistance voids 136 have been located in a section of the surgical clamp jaws starting near the pivot point and ending before a straight section at the tip of the clamp. Other embodiments may have different distributions of flexion assistance voids. As just two examples, FIGS. 8 and 9 illustrate embodiments of surgical clamp jaws 176 and 178 having examples of different flexion assistance void distribution. In FIG. 8, surgical clamp jaw 176 has flexion assistance voids 180 which are located near to the tip of the clamp jaw 176, while the clamp jaw 176 also has a straight section 182 nearer to the pivot point 184. Even with the straight section 182, the clamp jaw 176 still has a substantially concave inner profile 186 in the unclamped position illustrated in FIG. 8. The clamp jaw 176 also has a deflection control profile 188 opposite the inner profile 186. The features of deflection control profiles have been discussed previously.

In FIG. 9, surgical clamp jaw 178 has flexion assistance voids 190 which are distributed continuously between the pivot point 191 and the tip of the clamp jaw 178. The clamp jaw 178 has a substantially concave inner profile 192 in the unclamped position illustrated in FIG. 9. The clamp jaw 178 also has a deflection control profile 194 opposite the inner profile 192. The features of deflection control profiles have been discussed previously.

Figure 10:
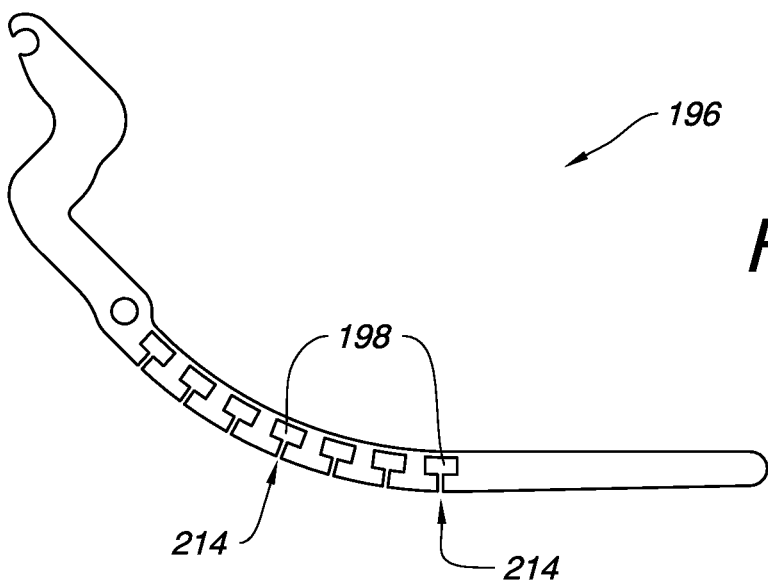
FIGS. 10-12 illustrate further embodiments of surgical clamp jaws featuring examples of different flexion assistance void shapes.
Figure 11:
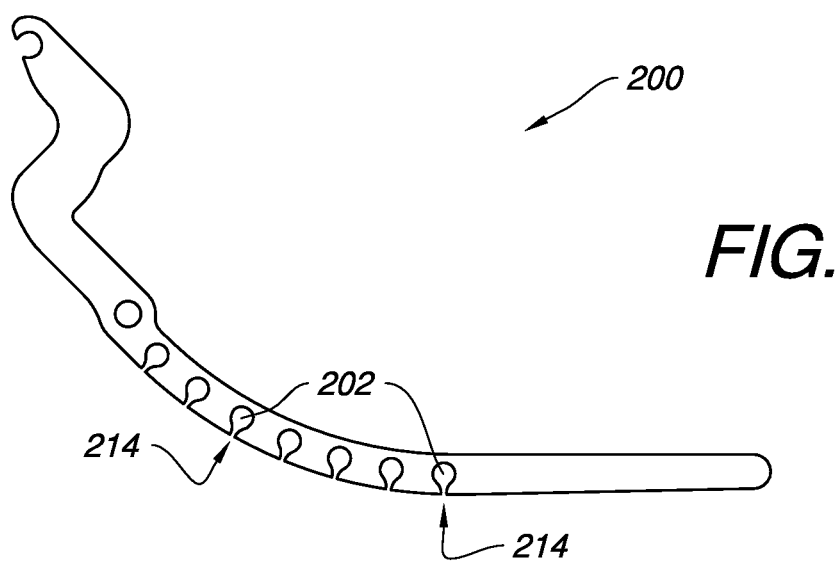
Figure 12:
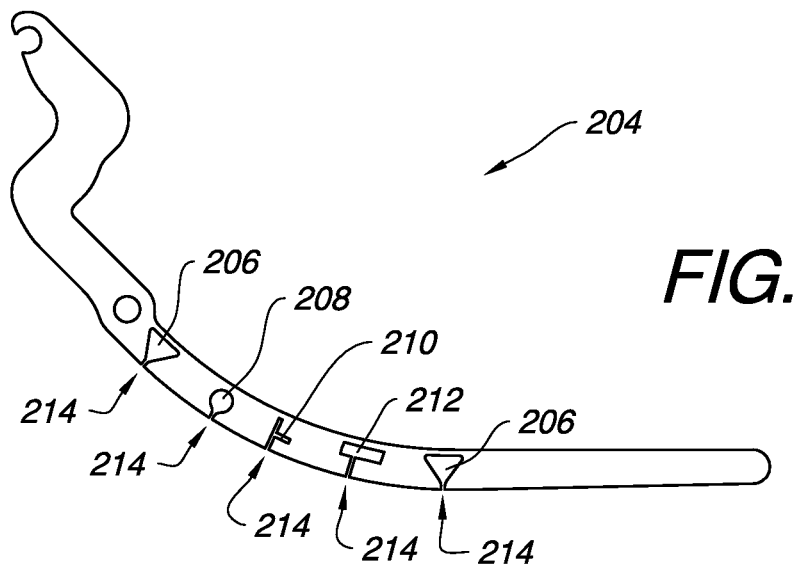

FIGS. 10-12 illustrate further embodiments of surgical clamp jaws featuring examples of different flexion assistance void shapes. Up to this point, the flexion assistance voids have been illustrated as substantially triangular, however, as has been noted above, the flexion assistance voids are not limited to one particular shape. For example, as with the surgical clamp jaw 196 illustrated in FIG. 10, the flexion assistance voids 198 are substantially rectangular. As another example, the surgical clamp jaw 200 illustrated in FIG. 11 has flexion assistance voids 202 which are substantially circular. Depending on the embodiment, the shapes of flexion assistance voids in a given surgical clamp jaw do not have to be uniform. As just one example, the surgical clamp jaw 204 illustrated in FIG. 12 has substantially triangular flexion assistance voids 206, a substantially circular flexion assistance void 208, and differently sized substantially rectangular assistance voids 210, 212. Other flexion assistance void shapes may be used in other embodiments.

Figure 13A:
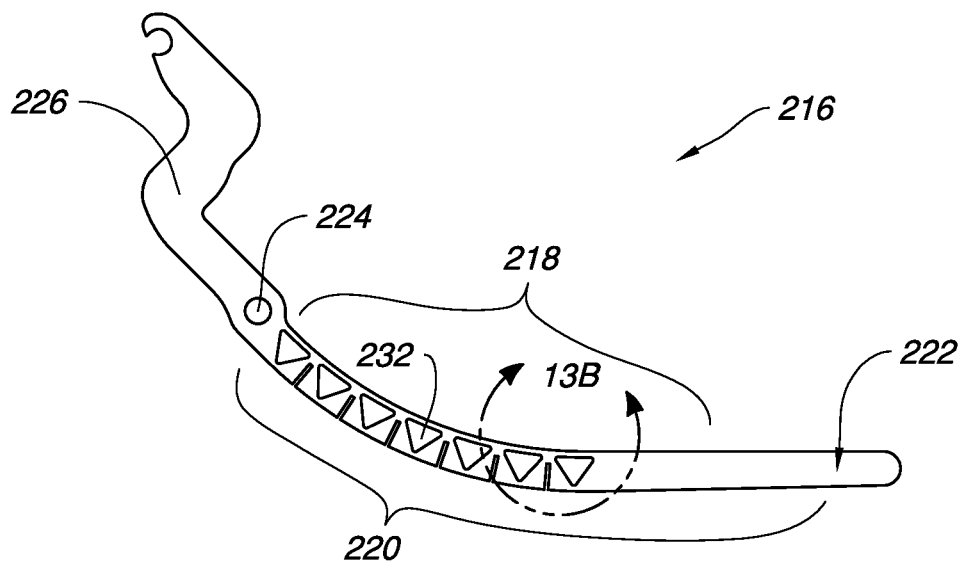
FIG. 13A illustrates another embodiment of a surgical clamp jaw where the sets of corresponding abutment surfaces are not contiguous with the flexion assistance voids.

In the embodiments of FIGS. 10-12, each flexion assistance void is in contact with a gap 214 between a set of corresponding abutment surfaces. However, depending on the embodiment, a flexion assistance void does not need to be in contact with a gap between corresponding abutment surfaces. For example, FIG. 13A illustrates one embodiment of a surgical clamp jaw 216 in an unclamped position. The surgical clamp jaw 216 has an inner profile 218 and a deflection control profile 220 opposite the inner profile 216. Although a portion 222 of the clamp jaw 216 has a straight profile, in this embodiment, when taking into account the totality of the inner profile 218, the inner profile 218 has a substantially concave profile in the unclamped position. The clamp jaw 216 also has a pivot point 224 and an arm 226 which can be used as an actuator or coupled to another actuator.

Figure 13B:
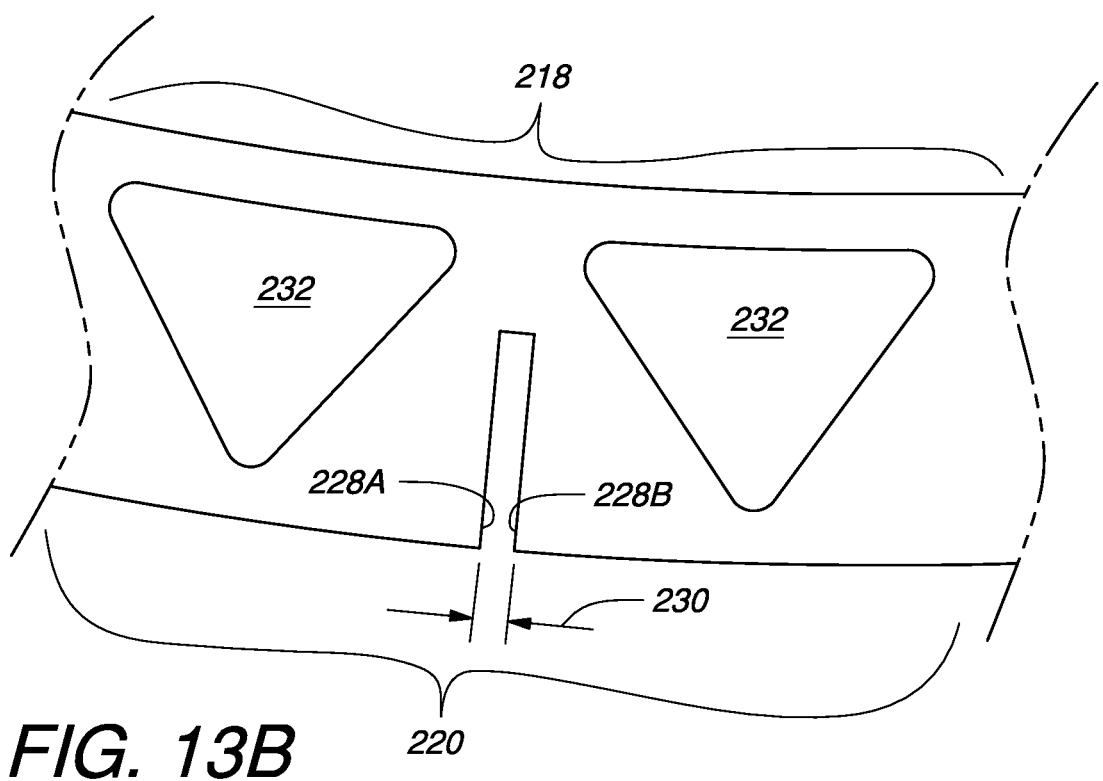
FIG. 13B is an enlarged view of a portion of the surgical clamp jaw of FIG. 13A.

In this embodiment, the deflection control profile 220 comprises one or more sets of corresponding abutment surfaces which are best seen in the enlarged view of FIG. 13B. FIG. 13B shows a set of corresponding abutment surfaces 228A, 228B. For convenience, only one set of corresponding abutment surfaces 228A, 228B will be discussed, however it should be understood that the other sets of corresponding abutment surfaces will operate in a similar fashion. In the unclamped position shown in FIG. 13B, the set of corresponding abutment surfaces 228A, 228B are not contacting each other. Instead, they are separated by an abutment separation distance 230. Depending on the embodiment, the abutment separation distance 230 between each set of corresponding abutment surfaces 228A, 228B may be the same or different. As the surgical clamp jaw 216 is moved from an unclamped position (shown in FIG. 13A) to a clamped position (not shown), the inner profile 218 will be able to deflect back towards the deflection control profile 220 until the abutment surfaces 228A, 228B come into contact with each other. As with previous embodiments, the abutment separation distance 230 can be established to control the amount of deflection possible for the inner profile 218. In this embodiment, the surgical clamp jaw 216 also has flexion assistance voids 232 which are not in contact with the gap 230 between a set of corresponding abutment surfaces 228A, 228B. The flexion assistance voids 232 will still serve to increase the flexibility of the inner profile 218.

Figure 14A:
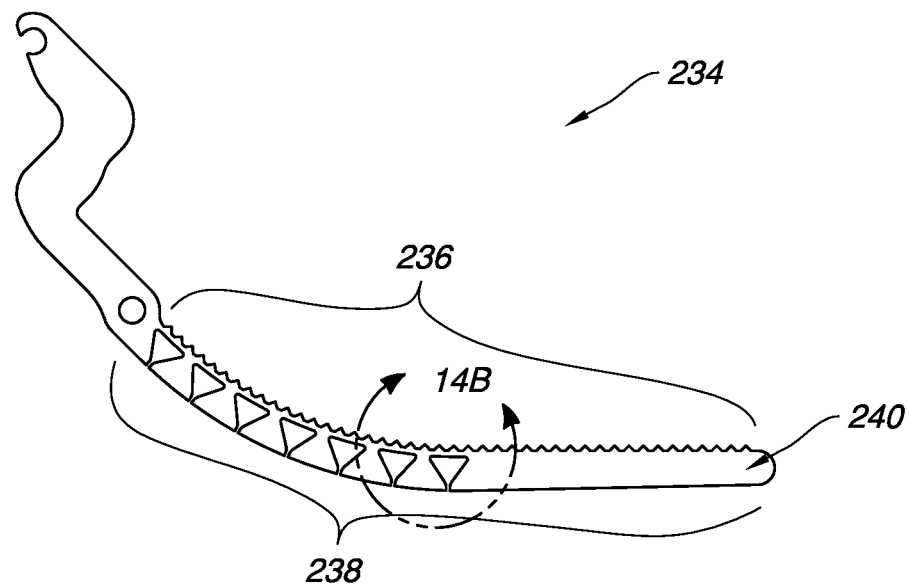
FIG. 14A illustrates an embodiment of the surgical clamp jaw of FIG. 5A also having an example of an integral gripping surface on the inner profile.

Although the inner profiles of the surgical clamp jaws illustrated to this point have had a smooth surface, other embodiments may have a rough surface for the inner profile. For example, FIG. 14A illustrates one embodiment of a surgical clamp jaw 234 in an unclamped position. The surgical clamp jaw 234 has an inner profile 236 and a deflection control profile 238 opposite the inner profile 236. In this embodiment, the inner profile 236 is textured. This could be useful, for example, to increase the grip of the inner profile 236.

Figure 14B:
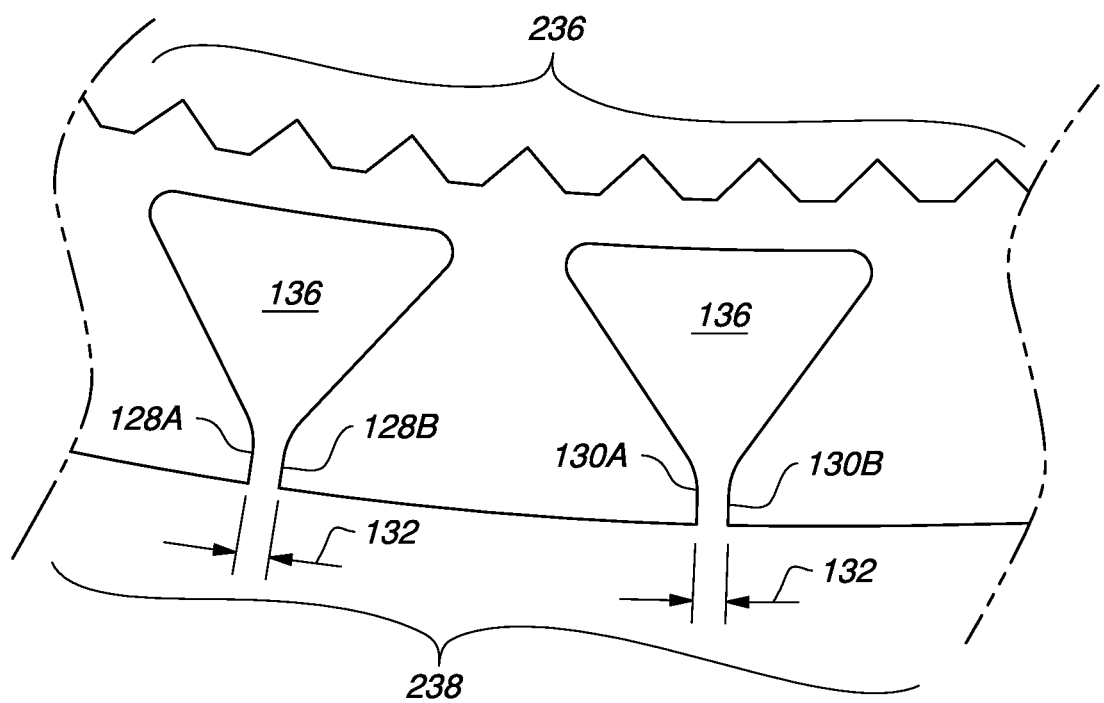
FIG. 14B is an enlarged view of a portion of the surgical clamp jaw of FIG. 14A.

Although a portion 240 of the clamp jaw is straight in this embodiment, when taking into account the totality of the inner profile 236, the inner profile 236 still has a substantially concave profile in the unclamped position. FIG. 14B shows an enlarged view of a portion of the surgical clamp jaw 234 of FIG. 14A. The remainder of the features of the surgical clamp jaw 234 are similar to the embodiments discussed previously and have corresponding element numbers.

The advantages of having a surgical clamp jaw with a concave inner profile in the unclamped position have been discussed above. These advantages include, but are not limited to, helping to prevent a conduit from being pushed out of the clamp as the clamp is tightened into a clamped position and helping to prevent the conduit from popping out of the clamp too soon as the clamp is opened (thereby giving surgeons more control over the release of the clamp). For embodiments where the clamp jaws need to be held in a clamped position without the need for a person holding the clamp shut, various locking elements can be applied to the clamp jaw actuators to help hold the clamp together. As just some examples, there are the ratchet features shown on the arms of the clamps in FIGS. 4A-4D, discussed previously. In some embodiments, however, it may be desirable to replace or supplement the actuator locking features with interlocking features located in one or more sets of corresponding abutment surfaces of the deflection control profile. As one example, FIG. 15A illustrates another embodiment of a surgical clamp jaw 242 having interlocking features (discussed below) on corresponding abutment surfaces. The surgical clamp jaw 242 has an inner profile 244 and a deflection control profile 246 opposite the inner profile 244. The inner profile 244 has a substantially concave profile in the unclamped position. The clamp jaw 242 also has a pivot point 248 and an arm 250 which can be used as an actuator or coupled to another actuator.

Figures 2, 15B:
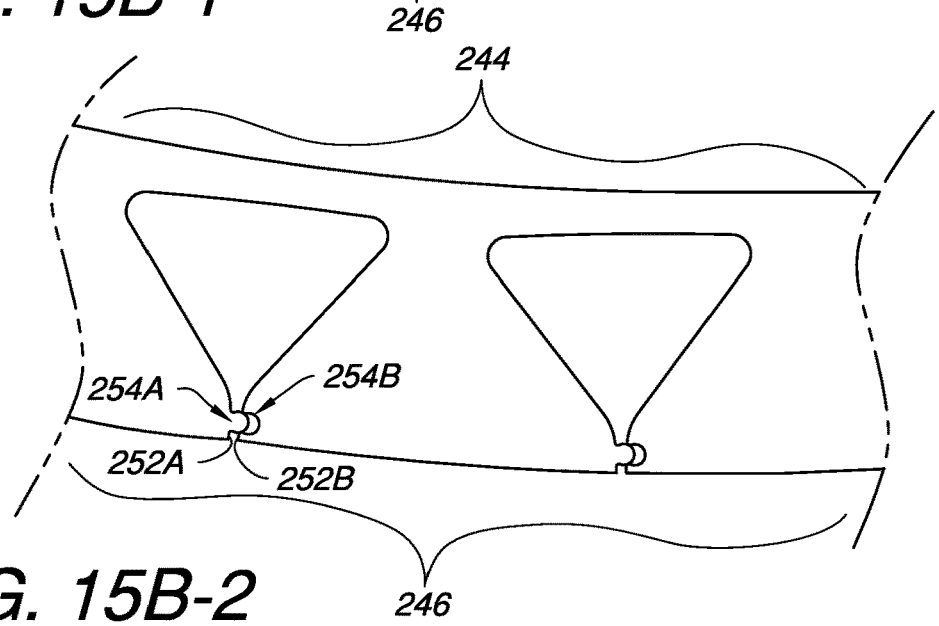

In this embodiment, the deflection control profile 246 comprises one or more sets of corresponding abutment surfaces which are best seen in the alternate enlarged views of FIGS. 15B-1 and 15B-2. The features of corresponding abutment surfaces have been discussed previously. Therefore, for convenience, only one set of corresponding abutment surfaces 252A, 252B will be discussed. It should be understood, however, that the other sets of corresponding abutment surfaces will operate in a similar fashion. In the embodiments illustrated in FIGS. 15B-1 and 15B-2, the first abutment surface 252A has a first interlocking feature 254A, while the second abutment surface 252B has a second interlocking feature 254B. In the embodiment of FIG. 15B-1 the first and second interlocking features 254A, 254B are not in contact with each other when the inner profile 244 is in an unclamped position. In the alternate embodiment of FIG. 15B-2, the first and second interlocking features 254A, 254B are contacting each other when the inner profile 244 is in an unclamped position. In either case, in the unclamped position, the abutment surfaces 252A, 252B are still separated and the first and second interlocking features are not interlocked.

As the surgical clamp jaw 242 is moved from an unclamped position (shown in FIG. 15A) to a clamped position (not shown), the inner profile 244 will be able to deflect back towards the deflection control profile 246 until the abutment surfaces 252A, 252B come into contact with each other. As the corresponding abutment surfaces 252A, 252B come together, the corresponding interlocking features 254A, 254B will also be forced together into an interlocking arrangement. This can help to offset the tendency of the inner profile 244 to want to return to a concave position, which may be desirable in some situations.

Figure 16A:
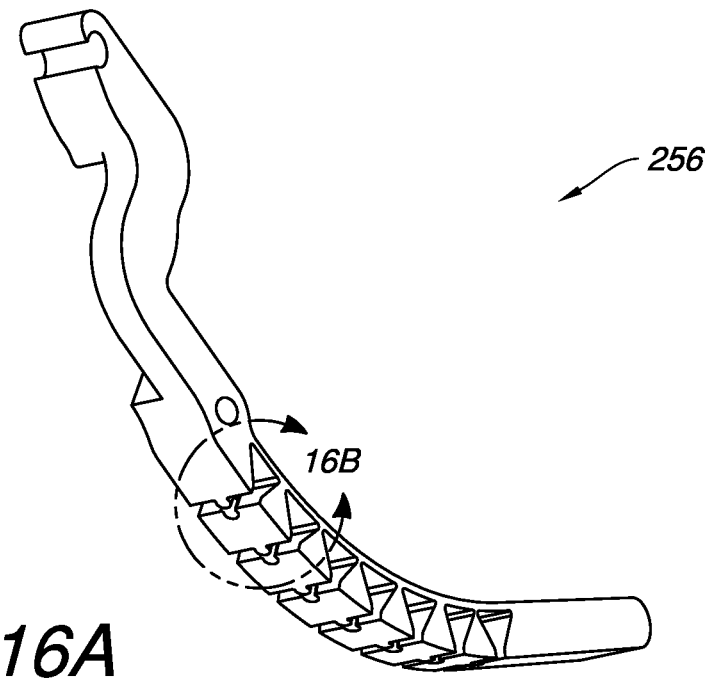
FIG. 16A illustrates a further embodiment of a surgical clamp jaw having interlocking features on corresponding abutment surfaces.
Figure 16B:
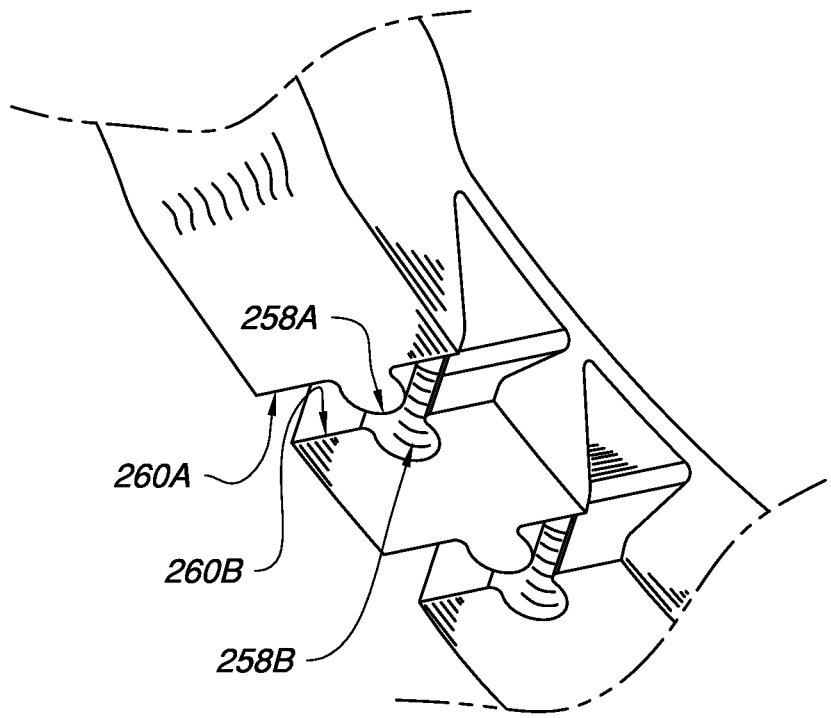
FIG. 16B is an enlarged view of a portion of the surgical clamp jaw of FIG. 16A.

FIG. 16A illustrates a further embodiment of a surgical clamp jaw 256 having a different arrangement of interlocking features 258A, 258B on corresponding abutment surfaces 260A, 260B. These features are best seen in the enlarged view of FIG. 16B which highlights a portion of the surgical clamp jaw 256 of FIG. 16A. The interlocking features 258A, 258B in this embodiment are oriented approximately ninety degrees from the interlocking features 254A, 254B of the previous embodiment. After seeing these examples, those skilled in the art will appreciate that other types of interlocking features in corresponding abutment surfaces are possible.

Figure 17A:
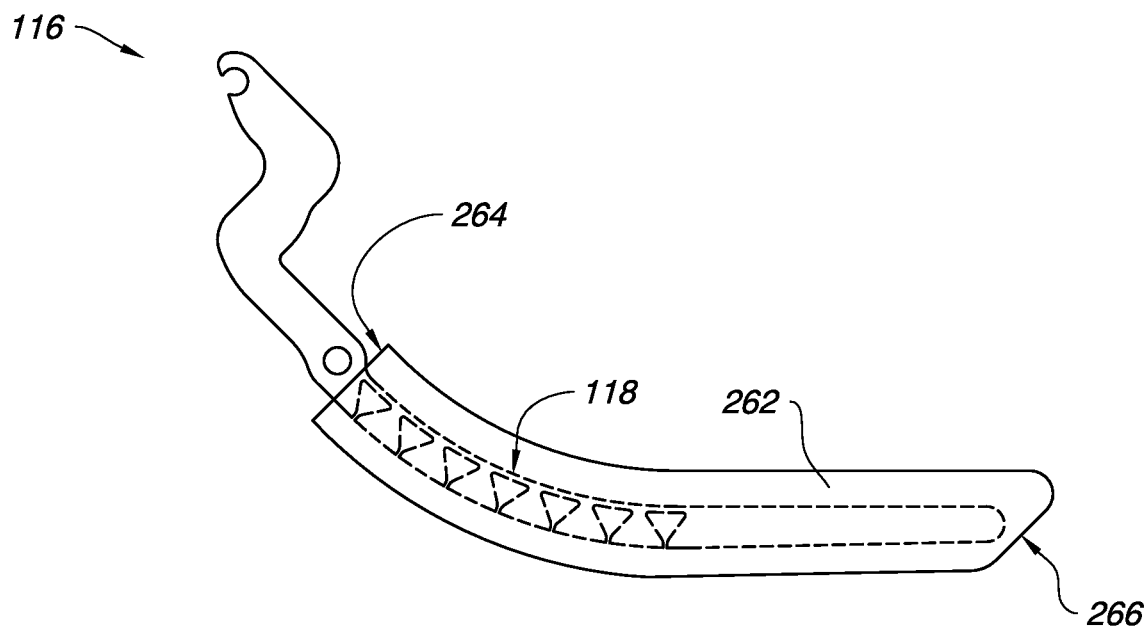
FIG. 17A illustrates the embodied surgical clamp jaw of FIG. 5A, in an unclamped position, with one embodiment of a shod.
Figure 17B:
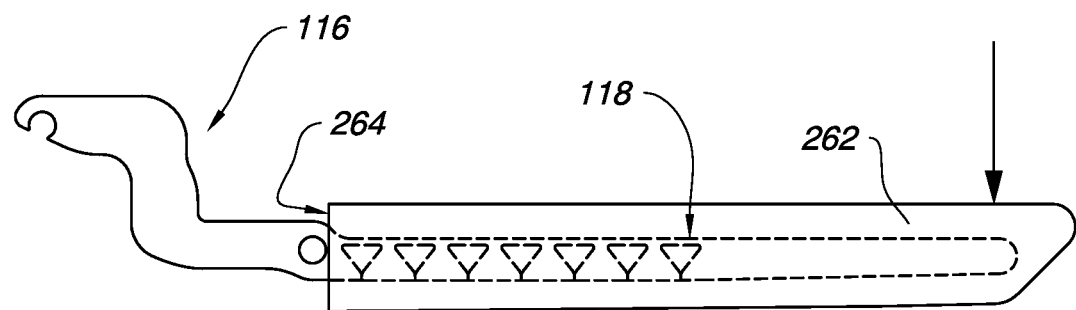
FIG. 17B illustrates the embodied surgical clamp jaw of FIG. 17A in a clamped position.

Up to this point, the surgical clamp jaw embodiments have been discussed and shown as if the inner profile of the clamp jaw would be in direct contact with any tissue that it is clamping. While such embodiments are very useful, it may also be advantageous to provide a shod (in this case a covering) for at least a portion of the clamp jaw. As one example, FIG. 17A illustrates the embodied surgical clamp jaw 116 of FIG. 5A (previously discussed), in an unclamped position, with one embodiment of a shod 262. The shod 262 has an opening 264 on a first end where the clamp jaw 116 may be inserted. In this embodiment, the opposite end 266 of the shod 262 is closed. FIG. 17B illustrates the embodied surgical clamp jaw 116 of FIG. 17A in a clamped position. The shod 262 is preferably flexible enough to move with the inner profile 118 as it changes shape moving from the unclamped position to the clamped position. The shod 262 (and all shod embodiments to be discussed herein) may be made from a wide variety of materials, including, but not limited to plastics, rubber, silicone, polymers, thermoplastics, resins, fabric, cotton, and fibers.

Figure 18A:
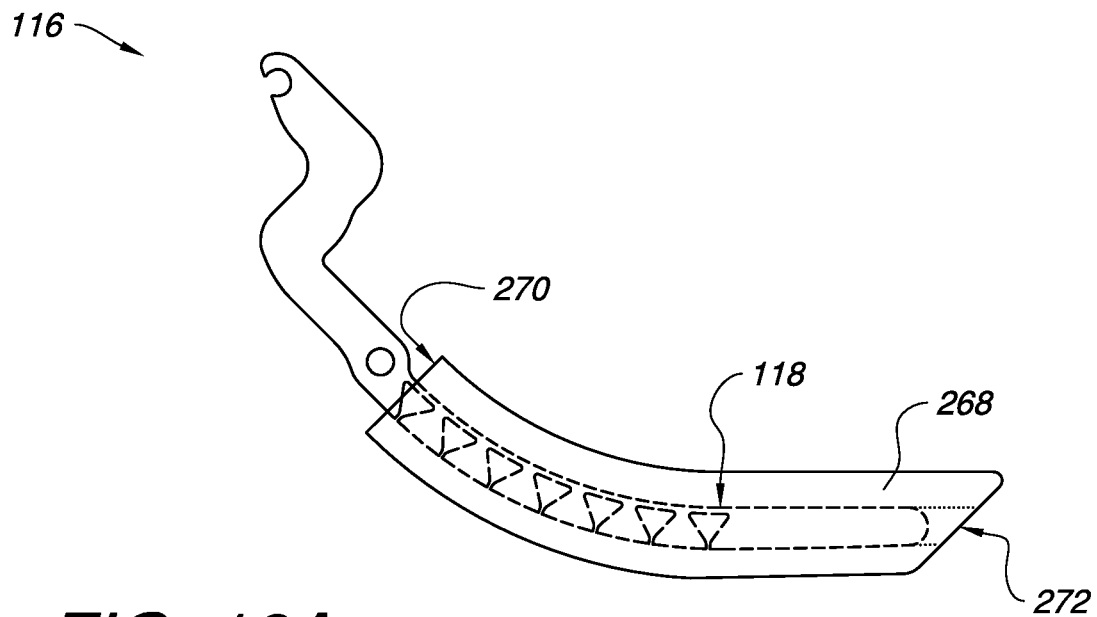
FIG. 18A illustrates the embodied surgical clamp jaw of FIG. 5A, in an unclamped position, with another embodiment of a shod.
Figure 18B:
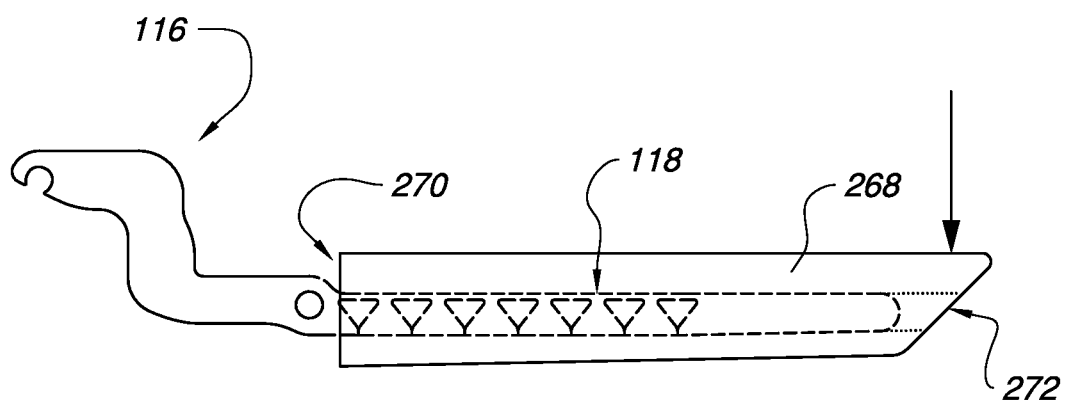
FIG. 18B illustrates the embodied surgical clamp jaw of FIG. 18A in a clamped position.

FIG. 18A illustrates the embodied surgical clamp jaw 116 of FIG. 5A (previously discussed), in an unclamped position, with another embodiment of a shod 268. The shod 268 has a first opening 270 on a first end where the clamp jaw 116 may be inserted. In this embodiment, the shod 268 also has a second opening 272 in a second end. In some embodiments, the second opening 272 may be a by-product of the fact that the shod could be manufactured from tubing that is cut to a particular length. In other embodiments, the second opening 272 may be specifically molded or formed. The second opening 272 can have the advantage of making the shod 268 easier to put on the surgical clamp jaw 116 since air cannot be caught and/or compressed into a closed end of the shod 268. FIG. 18B illustrates the embodied surgical clamp jaw 116 of FIG. 18A in a clamped position. The shod 268 is preferably flexible enough to move with the inner profile 118 as it changes shape moving from the unclamped position to the clamped position.

Figure 19:
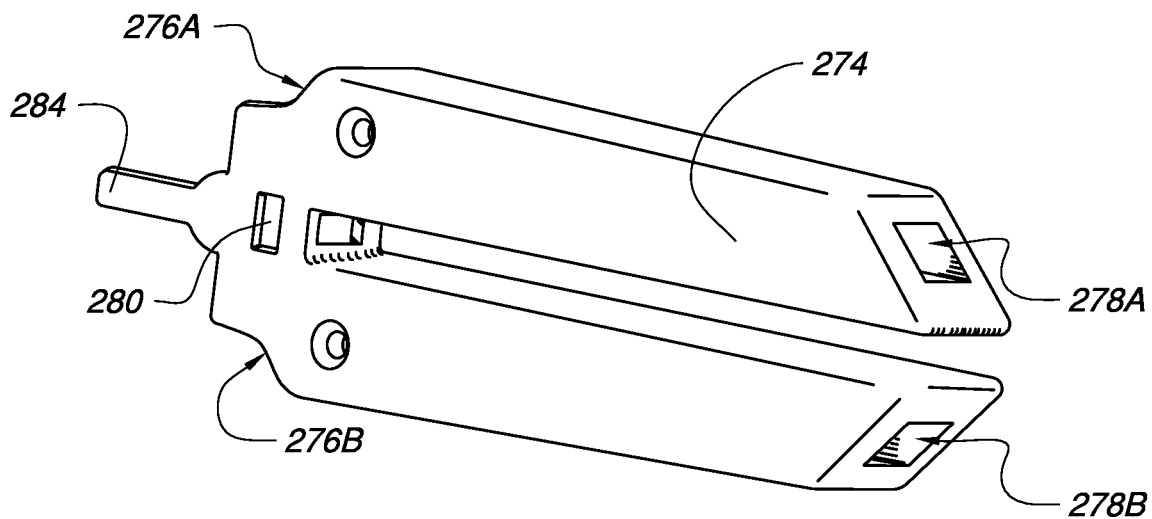
FIG. 19 illustrates an embodiment of a shod for a pair of surgical clamp jaws.
Figure 20:
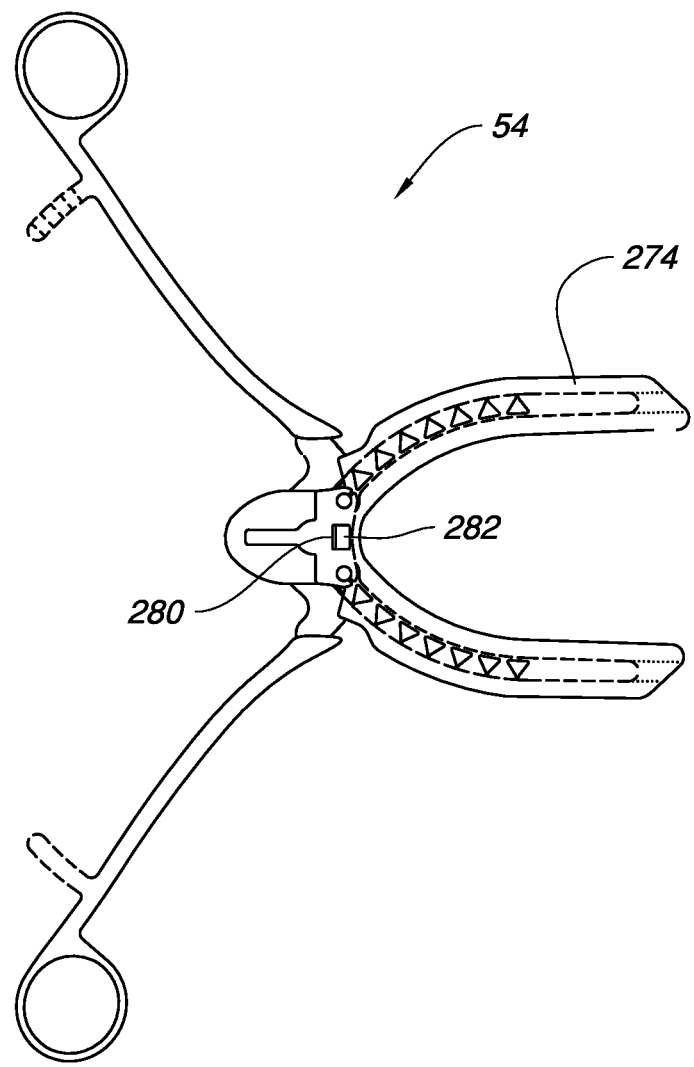
FIG. 20 illustrates the embodied surgical clamp of FIG. 2A with the embodied shod of FIG. 19.

Although clamp jaw shods have been discussed and shown to this point as being configured to fit a single clamp jaw, in other embodiments, a shod could be formed to cover more than one surgical clamp jaw. For example, FIG. 19 illustrates an embodiment of a shod 274 for a pair of surgical clamp jaws (not shown in this figure). Shod 274 has a first set of openings 276A, 276B (not visible from this angle) on a first end and a second set of openings 278A, 278B on a second end. FIG. 20 illustrates the embodied surgical clamp 54 of FIG. 2A with the embodied shod 274 of FIG. 19, showing that the shod 274 is able to flex with the surgical clamp jaws. The shod 274 may include a notch 280 which can be pulled over a corresponding feature 282 on the clamp 54 in order to help anchor the shod 274 in place. The shod 274 may also include a tab 284 to make it easier to install and remove the notch 280 from the corresponding feature 282 on the clamp 54.

Figure 21:
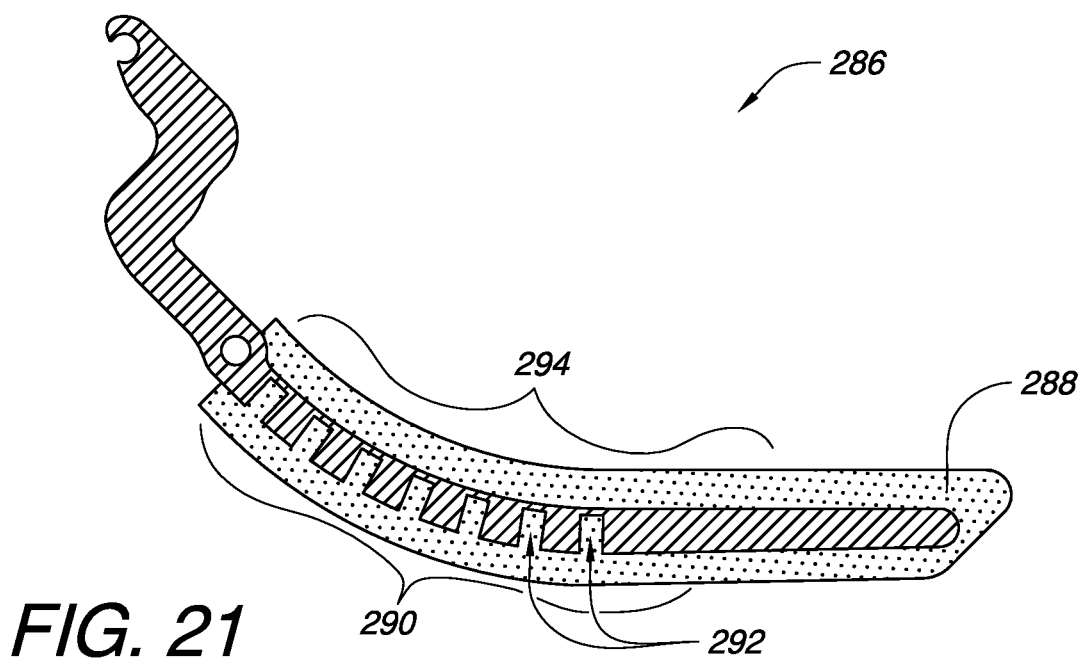
FIGS. 21 and 22 illustrate cross-sectional views of embodiments of a surgical clamp jaw having a shod, wherein the surgical clamp jaw has a deflection control profile defining gaps which are separated by portions of the shod.

At the beginning of this specification, one embodiment of a surgical clamp jaw was described as having an inner profile and a deflection control profile opposite the inner profile. In the ensuing embodiments discussed up to this point, the deflection control profile included one or more sets of corresponding abutment surfaces which are not in contact with each other when the inner profile is in an unclamped position, but are in contact with each other when the inner profile is in a clamped position. Other embodiments of a deflection control profile are possible, however. For example, FIG. 21 illustrates a cross-sectional view of an embodiment of a surgical clamp jaw 286 having a shod 288, wherein the surgical clamp jaw 286 has a deflection control profile 290 defining gaps 292 which are separated by portions of the shod 288. The clamp jaw 286 also has a substantially concave inner profile 294 opposite the deflection control profile 290. As the inner profile 294 is caused to deflect back towards the deflection control profile 290, the shod 288 material in the gaps 292 will be compressed. At some point, depending on the properties of the shod 288 material, the material in the gaps 292 will not compress further under normal clamping forces, and the inner profile will have a second profile shape in the clamped position. In this case, a shod 288 material may be chosen to compress in such a way that this second profile shape (not shown here) is substantially concave, substantially flat, or substantially convex.

Figure 22:
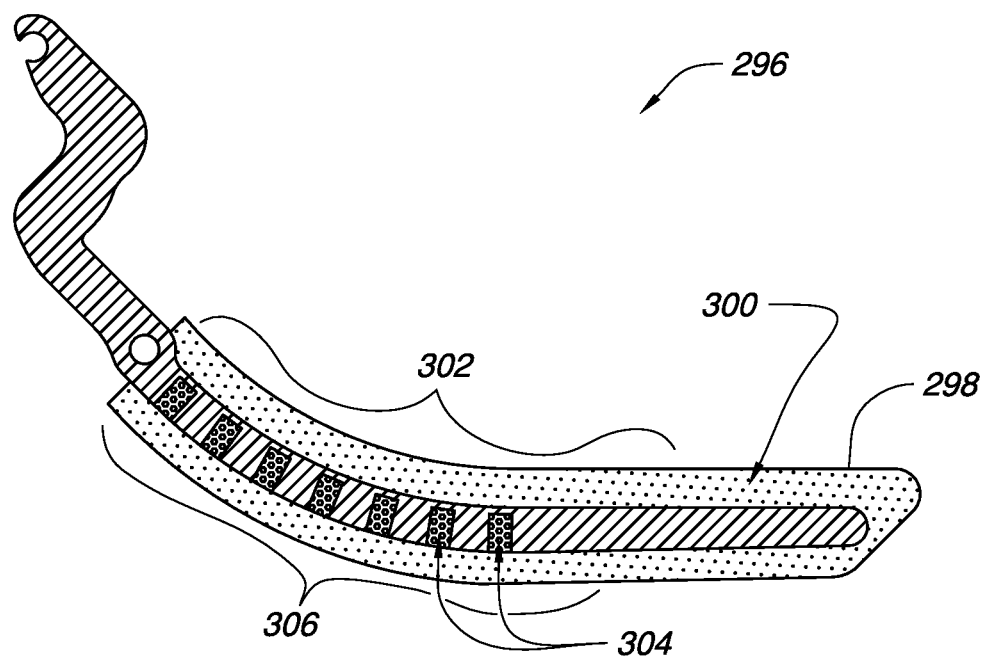

In some embodiments, the properties which might make for a good shod material (in terms of gripping ability, for example) might not make for a desired compression property in the gaps defined by the deflection control profile. In such a situation, the shod could include more than one material. For example, FIG. 22 illustrates a cross-sectional view of an embodiment of a surgical clamp jaw 296 having a shod 298 with a first material 300 at least over a portion of the inner profile 302. The shod 298 also has a second material 304 separating the gaps defined by the deformation control profile 306. Alternatively, this second material 304 could be separate from the first material 300 and therefore not part of the shod 298. The second material 304 may be selected for its compression properties independently of the properties of the first material 300. The inner profile 302 is substantially concave in the unclamped position illustrated in FIG. 22. As the inner profile 302 is caused to deflect back towards the deflection control profile 306, the second material 304 in the gaps of the deflection control profile 306 will be compressed. At some point, depending on the properties of the second material 304, the second material 304 will not compress further under normal clamping forces, and the inner profile 302 will have a second profile shape in the clamped position. In this case, the second material 304 may be chosen to compress in such a way that this second profile shape (not shown here) is substantially concave, substantially flat, or substantially convex.

Various advantages of a surgical clamp and clamp jaw have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical device, comprising:
   a first clamp jaw;
   a second clamp jaw rotatably coupled to the first clamp jaw such that the first clamp jaw and the second clamp jaw pivot between a first unclamped position and a second clamped position, the second clamp jaw comprising:
   an inner profile; and
   a deflection control profile opposite the inner profile, wherein the deflection control profile comprises a first abutment surface formed in the second clamp jaw and a second abutment surface formed in the second clamp jaw,
   wherein in the first unclamped position, the first abutment surface is disposed remote from the second abutment surface, and wherein in the second clamped position, all or a portion of the first abutment surface contacts all or a portion of the second abutment surface, and
   in the first unclamped position, the inner profile of the second clamp jaw has a first shape and in the second clamped position, the inner profile of the second clamp jaw has a second shape that is substantially linear.

2. The surgical device of claim 1, the second clamp jaw further comprising a flexion assistance void formed in the second clamp jaw, wherein the flexion assistance void is defined by one or more surfaces.

3. The surgical device of claim 2, wherein a first portion of the one or more surfaces defining the flexion assistance void is in contact with or adjacent to a portion of a surface at least partially defining the first abutment surface.

4. The surgical device of claim 3, wherein a second portion of the one or more surfaces defining the flexion assistance void is in contact with or adjacent to a portion of a surface at least partially defining the second abutment surface.

5. The surgical device of claim 4, wherein a first planar surface at least partially defines the first abutment surface and a second planar surface at least partially defines the second abutment surface, wherein in the first unclamped position, the first planar surface and the second planar surface cooperate to define a slot formed in the second clamp jaw.

6. The surgical device of claim 2, wherein the flexion assistance void is defined by a plurality of surfaces, and the plurality of surfaces cooperate to form a substantially triangular shape.

7. The surgical device of claim 1, wherein the inner profile comprises a smooth surface.

8. The surgical device of claim 1, the second clamp jaw further comprising a plurality of flexion assistance voids formed in the second clamp jaw, and wherein each of the plurality of flexion assistance voids is defined by one or more surfaces.

9. The surgical device of claim 1, wherein the first abutment surface and the second abutment surface define a first set of abutment surfaces formed in the second clamp jaw, and the deflection control profile comprises at least a second set of abutment surfaces and a third set of abutment surfaces.

\* \* \* \* \*